United States Patent
Qin et al.

(10) Patent No.: US 9,738,733 B2
(45) Date of Patent: Aug. 22, 2017

(54) POLYMERS INCORPORATING HYDROXYL GROUP-CONTAINING METHYLSTYRENE

(71) Applicants: Zengquan Qin, Copley, OH (US); Yuan-Yong Yan, Copley, OH (US); Xiao-Dong Pan, Houston, TX (US)

(72) Inventors: Zengquan Qin, Copley, OH (US); Yuan-Yong Yan, Copley, OH (US); Xiao-Dong Pan, Houston, TX (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 15/265,532

(22) Filed: Sep. 14, 2016

(65) Prior Publication Data

US 2017/0002105 A1    Jan. 5, 2017

Related U.S. Application Data

(62) Division of application No. 14/718,078, filed on May 20, 2015, now Pat. No. 9,469,661, which is a division of application No. 13/701,056, filed as application No. PCT/US2011/038467 on May 28, 2011, now Pat. No. 9,051,455.

(60) Provisional application No. 61/349,947, filed on May 31, 2010.

(51) Int. Cl.

| | |
|---|---|
| *C08F 12/14* | (2006.01) |
| *C08K 3/04* | (2006.01) |
| *C08K 3/36* | (2006.01) |
| *C08L 19/00* | (2006.01) |
| *C08C 19/44* | (2006.01) |
| *C07F 7/18* | (2006.01) |
| *C08F 36/04* | (2006.01) |
| *C08F 236/10* | (2006.01) |
| *C08L 15/00* | (2006.01) |
| *C08L 9/06* | (2006.01) |
| *B60C 1/00* | (2006.01) |
| *C08F 212/14* | (2006.01) |
| *C08L 7/00* | (2006.01) |

(52) U.S. Cl.
CPC ............ *C08C 19/44* (2013.01); *B60C 1/0016* (2013.04); *C07F 7/1852* (2013.01); *C08F 12/14* (2013.01); *C08F 36/04* (2013.01); *C08F 236/10* (2013.01); *C08K 3/04* (2013.01); *C08K 3/36* (2013.01); *C08L 9/06* (2013.01); *C08L 15/00* (2013.01); *C08L 19/006* (2013.01); *C08F 212/14* (2013.01); *C08K 2003/045* (2013.01); *C08L 7/00* (2013.01); *C08L 2310/00* (2013.01); *Y02P 20/55* (2015.11)

(58) Field of Classification Search
None
See application file for complete search history.

(56) References Cited

U.S. PATENT DOCUMENTS

| | | | | |
|---|---|---|---|---|
| 4,025,401 | A * | 5/1977 | Fujiwara | ............... C08F 255/00 204/296 |
| 6,022,665 | A * | 2/2000 | Watanabe | ............. C08F 212/14 430/270.1 |

* cited by examiner

*Primary Examiner* — Vu A Nguyen
(74) *Attorney, Agent, or Firm* — Meredith E. Hooker; David G. Burleson

(57) ABSTRACT

Vulcanizates with desirable properties can be obtained from compounds incorporating polymers that include hydroxyl group-containing α-methylstyrene functionalities. The functionalities can be incorporated by using any or all of appropriate initiators, monomers and optional terminating compounds. Such polymers exhibit excellent interactivity with both conventional and non-conventional fillers.

20 Claims, No Drawings

POLYMERS INCORPORATING HYDROXYL GROUP-CONTAINING METHYLSTYRENE

CROSS-REFERENCE TO RELATED APPLICATIONS

This application is a division of U.S. patent application Ser. No. 14/718,078, now issued as U.S. Pat. No. 9,469,661, which was a division of 13/701,056, now issued as U.S Pat. No. 9,051,455, which was a national stage entry of international appl. PCT/US2011/038467, which was filed 28 May 2011 and which claimed the benefit of U.S. provisional patent application no. 61/349,947, filed 31 May 2010, the entire disclosures of which are incorporated by reference herein.

BACKGROUND INFORMATION

Rubber goods such as tire treads often are made from elastomeric compositions that contain one or more reinforcing materials such as, for example, particulate carbon black and silica; see, e.g., *The Vanderbilt Rubber Handbook*, 13th ed. (1990), pp. 603-04.

Good traction and resistance to abrasion are primary considerations for tire treads; however, motor vehicle fuel efficiency concerns argue for a minimization in their rolling resistance, which correlates with a reduction in hysteresis and heat build-up during operation of the tire. These considerations are, to a great extent, competing and somewhat contradictory: treads made from compositions designed to provide excellent road traction, particularly in wet conditions, tend to exhibit increased rolling resistance while those designed to minimize rolling resistance might provide only acceptable traction performance.

Filler(s), polymer(s), and additives typically are chosen so as to provide an acceptable balance of these properties. Ensuring that reinforcing filler(s) are well dispersed throughout the polymeric material(s) both enhances processability and acts to improve physical properties. Dispersion of fillers can be improved by increasing their interaction with the polymer(s) and/or decreasing their interaction with each other. Examples of efforts of this type include high temperature mixing in the presence of selectively reactive promoters, surface oxidation of compounding materials, surface grafting, and chemically modifying the polymer, typically at a terminus thereof.

Many of the polymers used in the manufacture of vulcanizates such as, e.g., tire components, are elastomeric. In addition to natural rubber, some of the most commonly employed include high-cis polybutadiene, often made by processes employing Ziegler-Natta catalysts, and substantially random styrene/butadiene interpolymers, often made by processes employing anionic initiators. Chemical modifications that can be undertaken with carbanionic polymers often do not work for polymers made via catalytic processes.

SUMMARY

In a first general aspect is provided a compound having the general formula

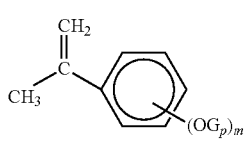

(I)

where each $G_p$ independently is a protecting group (defined below) and m is an integer of from 1 to 5 inclusive.

In another aspect is provided a method of making a formula I-type compound. The method involves nucleophilic addition of an alkylene group, commonly a methylene group, to the carbonyl group of an acetophenone having the general formula

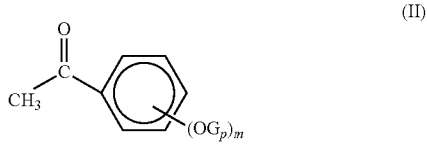

(II)

where $G_p$ and m are defined as above. The nucleophilic addition can be accomplished by a Wittig reaction involving an ylide, typically an alkyltriphenylphosphonium ylide such as methyltriphenylphosphonium ylide, with the acetophenone. (An ylide can be generated by a reaction of, e.g., an alkyltriphenylphosphonium halide and an alkali metal hydrocarbyl.)

In yet another aspect is provided a method of using a formula I-type compound in a polymerization. The method can involve employing an anionic version of a formula I compound as an initiator or employing a formula I compound as a monomer. Where a formula I compound is polymerized after essentially all other monomers have been converted, the mer derived from a formula I compound can constitute one or more terminal units of the polymer chain. Any such terminal unit that remains living (active) can be quenched without further functionalization or can be reacted with a terminating compound which might provide particulate interactivity supplemental to or complementary with that available from the unit(s) themselves.

In a still further aspect is provided a functionalized polymer that includes polyene mer and at least one unit having the general formula

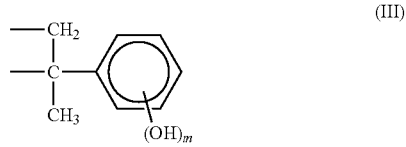

(III)

where m is defined as above. The unit can be the initial unit of a polymer chain (i.e., derived from a lithiated version of a formula I compound acting as a functional initiator) or one or more such units can be present along the polymer chain, optionally located at a terminus of the polymer chain, optionally also directly bonded to a functional group. The hydroxyl group(s) can be provided by hydrolyzing the protecting group(s) from a formula I compound.

In situations where one or more formula III units is or are incorporated after essentially all other mer, i.e., at or near the end of polymerization, the polymer can have the general formula

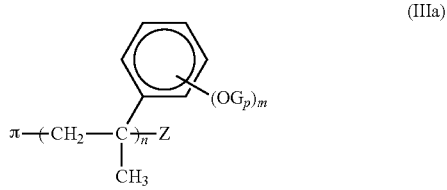

(IIIa)

where π is a polymer that includes polyene mer, each of $G_p$ and m is defined as above, n is an integer of from 1 to 10, alternatively from 1 to 5, alternatively from 1 to 3, inclusive, and Z is a hydrogen atom or the radical (defined below) of a terminating compound (defined below). Where a carbanionic polymer is reacted with a formula I compound, a formula IIIa polymer can be provided by quenching, which results in Z being a hydrogen atom, or by reaction with a terminating compound, which results in Z being the radical of terminating compound.

Alternatively, a formula I compound can be reacted with a hydrocarbyl alkali metal compound so as to provide an ionic compound having the general formula

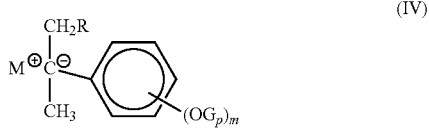

(IV)

where M is an alkali metal atom and R is a hydrocarbyl group such as alkyl, cycloalkyl, aryl, etc.; a formula IV compound can be used to initiate polymerization of any of a variety of ethylenically unsaturated mer with chain propagation beginning at the anionic carbon atom of formula IV, which results in incorporation of the formula III unit at the beginning of polymerization (i.e., the initiating end of the polymer).

In other aspects are provided methods of making formula IV compounds, methods of using formula IV compounds to initiate polymerization of ethylenically unsaturated monomers, methods of making formula IIIa polymers, and methods of providing and using polymers containing formula III units, particularly those represented formula III.

In any of the foregoing aspects, the protecting group(s) can be replaced, typically via hydrolysis, with hydrogen atoms so as to provide one or more hydroxyl substituents directly bonded to the phenyl group. This can result in m (defined above) hydroxyl substituents being directly bonded to the phenyl group.

The carbanionic polymer can be provided by anionically initiating polymerization of ethylenically unsaturated monomers, which typically include one or more types of polyenes, particularly conjugated dienes. Where a polyene is one of the types of monomers employed, the polymer can include unsaturation within and/or pendent from the polymer chain; this unsaturation preferably is substantially random along the polymer chain. The resulting polymer can include multiple mer resulting from incorporation of alkenes (A units) and one or more mer defined by general formula III (B units). In certain embodiments, the polymer also can include directly bonded aromatic pendent groups (C units). In these and/or other embodiments, the polymer can be substantially linear.

Regardless of how characterized, the polymer can interact with particulate filler such as, e.g., carbon black and silica. Compositions, including vulcanizates, that include particulate fillers and such polymers also are provided, as are methods of providing and using such compositions.

Other aspects of the invention will be apparent to the ordinarily skilled artisan from the description of illustrative embodiments that follows. To assist in understanding that description, certain definitions are provided immediately below. These are intended to apply throughout unless the surrounding text explicitly indicates a contrary intention:

"polymer" means the polymerization product of one or more monomers and is inclusive of homo-, co-, ter-, tetra-polymers, etc.;

"mer" or "mer unit" means that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetrapolymers, and the like;

"random interpolymer" means an interpolymer having mer units derived from each type of constituent monomer incorporated in an essentially non-repeating manner and being substantially free of blocks, i.e., segments of three or more of the same mer;

"carbanionic" and "living" are used interchangeably;

"gum Mooney viscosity" is the Mooney viscosity of an uncured polymer prior to addition of any filler(s);

"compound Mooney viscosity" is the Mooney viscosity of a composition that includes, inter alia, an uncured or partially cured polymer and particulate filler(s);

"substituted" means one containing a heteroatom or functionality (e.g., hydrocarbyl group) that does not interfere with the intended purpose of the group in question;

"directly bonded" means covalently attached with no intervening or interposed atoms or groups;

"polyene" means a molecule with at least two double bonds located in the longest portion or chain thereof, and specifically is inclusive of dienes, trienes, and the like;

"polydiene" means a polymer that includes mer units from one or more dienes;

"phr" means parts by weight (pbw) per 100 pbw rubber;

"protecting group" means a group that (1) is sufficiently reactive toward the oxygen atom of a hydroxyl functionality that, under a first set of reaction conditions, it can replace the H atom of that group, (2) is non-reactive toward carbanionic polymers and the initiators used to provide them, and, optionally, (3) can be replaced by a H atom under a second set of reaction conditions which differ from the first set;

"radical" means the portion of a molecule that remains after reacting with another molecule, regardless of whether any atoms are gained or lost as a result of the reaction;

"terminating compound" means a chemical compound that includes at least one heteroatom, including but not limited to N, Si, O or S, and that is capable of reaction with a carbanionic polymer so as to provide a group or moiety that provides enhanced interactivity with at least one type of particulate filler;

"terminus" means an end of a polymeric chain; and

"terminal moiety" means a group or functionality located at a terminus.

All values herein in the form of percentages are weight percentages unless the surrounding text explicitly indicates a contrary intention. The relevant portion(s) of any specifically referenced patent and/or published patent application are incorporated herein by reference.

DESCRIPTION OF ILLUSTRATIVE EMBODIMENTS

Compounds defined by formula I can be provided from the corresponding formula II-type compounds via a Wittig reaction employing an alkyltriphenylphosphonium ylide, typically methyltriphenylphosphonium ylide. (Alkyl groups other than methyl provide a formula I compound with the vinyl carbon atom being substituted, i.e., an alkyl group in place of one of the hydrogen atoms.) This type of nucleophilic addition, where a carbonyl oxygen atom is replaced with a methylene group so as to result in a styrenic compound, is specifically exemplified below in the examples; that description includes specific reaction conditions from which an ordinarily skilled artisan can envision multiple variations and alternatives.

A formula I-type compound can be used in a number of ways to provide a functionalized polymer. Generally, such polymers can include mer derived from one or more polyenes, particularly dienes, and terminal functionality and/or one or more mer units resulting from (directly or indirectly) incorporation of a formula I compound. In at least certain embodiments, the polymer also can include directly bonded pendent aromatic groups.

A polymer having a B unit can be provided by reacting a formula I compound with a polymer having an active chain end, either during or at the conclusion of chain propagation. Alternatively or additionally, a formula I compound can be reacted with a hydrocarbyl alkali metal compound so as to provide an ionic compound capable of initiating polymerization of ethylenically unsaturated monomers, i.e., a formula IV initiator. Accordingly, one or more B units can be located along the polymer chain, optionally in a small (1-5 unit) block, or at a terminus, and/or a radical of a formula IV initiator can be located at a terminus. Where at least one B unit is located at a polymer chain terminus, the result is a formula IIIa-type functionalized polymer with the identity of Z depending on whether the polymer is subjected to further functionalization through reaction with a terminating compound.

The following describes the production and use of a polymer that includes multiple A mer, i.e., alkene units; optionally, multiple C mer, i.e., units that include a pendent aryl group, particularly a phenyl group; and at least one B mer. Each of the A, B and C mer can result from incorporation of ethylenically unsaturated monomers.

The A mer typically result from incorporation of polyenes, particularly trienes (e.g., myrcene) and dienes, particularly $C_4$-$C_{12}$ dienes and even more particularly conjugated dienes such as 1,3-butadiene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, isoprene, 4-methyl-1,3-pentadiene, 2,4-hexadiene, and the like. Some or all of the A mer can be derived from one or more types of dienes, particularly one or more types of conjugated dienes, e.g., 1,3-butadiene. In some embodiments, essentially all (i.e., at least 95%) of the polyenes can be dienes, particularly conjugated dienes. Such polymers typically display elastomeric characteristics.

Polyenes can incorporate into polymeric chains in more than one way. Especially for tire tread applications, controlling this manner of incorporation can be desirable. A polymer chain with an overall 1,2-microstructure, given as a numerical percentage based on total number of polyene units, of from ~10 to ~80%, optionally from ~25 to ~65%, can be desirable for certain end use applications. A polymer that has an overall 1,2-microstructure of no more than ~50%, preferably no more than ~45%, more preferably no more than ~40%, even more preferably no more than ~35%, and most preferably no more than ~30%, based on total polyene content, is considered to be substantially linear. For certain end use applications, keeping the content of 1,2-linkages even lower, e.g., to less than ~7%, less than 5%, less than 2%, or less than 1%, can be desirable.

Depending on the intended end use, one or more of the polymer chains can include pendent aromatic groups, which can be provided by C mer, i.e., mer derived from vinyl aromatics, particularly the $C_8$-$C_{20}$ vinyl aromatics such as, e.g., styrene, α-methyl styrene, p-methyl styrene, the vinyl toluenes, and the vinyl naphthalenes. When used in conjunction with one or more polyenes, C mer can constitute from ~1 to ~50%, from ~10 to ~45%, or from ~20 to ~40% of the polymer chain; random microstructure can provide particular benefit in some end use applications such as, e.g., rubber compositions used in the manufacture of tire treads. Where a block interpolymer is desired, C units can constitute from ~1 to ~90%, generally from ~2 to ~80%, commonly from ~3 to ~75%, and typically ~5 to ~70% of the polymer chain. (All percentages in this paragraph are mole percentages.)

Exemplary interpolymers include those in which one or more conjugated dienes provide the A units, i.e., polydienes; among these, 1,3-butadiene can be one of several or the only polyene employed. Where C units are desired, they can be provided from styrene so as to provide, for example, SBR. In each of the foregoing types of exemplary interpolymers, one or more B units also are incorporated.

A B unit, generally defined by formula III, includes a pendent phenyl group that includes one or more directly bonded hydroxyl groups. Because the H atoms of hydroxyl groups are active and can interfere with certain polymerization processes (i.e., quench a carbanionic polymer), the B unit(s) typically are provided from compounds that include protecting groups, identified above as $G_p$. Although each $G_p$ moiety need not be identical, ease and simplicity typically result in a single type of $G_p$ moiety for a given compound.

Unless a particular $G_p$ constitutes a moiety that is capable of enhancing the polymer's interactivity with particulate filler (as evidenced by, for example, reduced tan δ values at 50° C.), it preferably also is capable of being hydrolyzed by a process that does not destroy or otherwise react with ethylenic unsaturation in the polymer resulting from the presence of A units. Trihydrocarbylsilyl groups are a non-limiting example of the type of $G_p$ moiety that can serve these dual purposes; such moieties can be provided by reacting the hydroxyl substituent(s) of the phenyl group with a trihydrocarbylsilyl halide, preferably a trialkylsilyl halide. In addition to trihydrocarbylsilyl moieties, other potentially useful $G_p$ moieties include but not limited to benzyl, t-butyl, alkoxyalkyl (e.g., $CH_3OCH_2$—), tetra-hydropyranyl, allyl, sulfonamide, and bulky esters (e.g., pivalates).

The phenyl group in a single B unit, prior to hydrolysis, includes one (m=1) or more (2≤m≤5) $OG_p$ moieties. Relative to the point of attachment of the phenyl group to the polymer chain, a single $OG_p$ moiety can be located ortho, meta, or para on the phenyl ring, while multiple $OG_p$ moieties can be provided 2,3-, 2,4-, 2,5-, 2,6-, 3,4-, 3,5-, 3,6-, 2,3,4-, 2,3,5-, etc., on the phenyl ring. Additionally, where a polymer includes more than one B unit, each unit can have different numbers of $OG_p$ moieties and/or have $OG_p$ moieties at different positions on their phenyl groups.

B units typically are provided from formula I compounds in which m is an integer of from 1 to 5 inclusive, i.e., an α-methylstyrene compound in which the phenyl group includes at least one $OG_p$ moiety and up to five such moieties. In one embodiment, two $OG_p$ moieties can be present, optionally bonded to adjacent ring C atoms, e.g., at the 3 and 4 positions, of the phenyl group.

When one or more formula I-type compounds is polymerized, it/they provide the B unit(s). The number of B units typically is small relative to the number of A units and, if present, C units; a relatively small number of B units has been found to provide a satisfactory level of desirable properties, with further improvements in those properties not necessarily being proportional to the number of B units present. This relatively small number can be expressed in a number of ways. For example, the weight percentage of the final polymer attributable to B units commonly is less than 2%, more commonly from ~0.05 or ~0.1 to ~1.5%, and typically from ~0.1 or ~0.2 to ~1.0%. The percentage of B mer relative to the total number of mer in the polymer commonly is less than 1%, more commonly from ~0.01 to ~0.75%, and typically from ~0.05 to ~0.5%. The total number of B units in a given polymer generally is from 1 to ~30, commonly from 1 to 12, more commonly from 1 to 10, and most commonly from 1 to 5.

The B unit(s) can incorporated near the beginning of the polymerization, near the end of the polymerization, or at any one or more intermediate points, taking into account the relative reactivity of the formula I compound(s) vis-à-vis those of other types of ethylenically unsaturated compounds employed in the polymerization; in the first two of the foregoing possibilities, a B unit can be provided within 6 chain atoms of, within 2 units of, adjacent to a terminus of the polymer, or as a terminal unit. Where more than one B unit is present, they typically are adjacent one another, at or near the terminus of a polymer chain.

The foregoing types of polymers can be made by emulsion polymerization or solution polymerization, with the latter affording greater control with respect to such properties as randomness, microstructure, etc. Solution polymerizations have been performed for many decades, so the general aspects thereof are known to the ordinarily skilled artisan, so only certain general aspects are provided here for convenience of reference.

Both polar solvents, such as THF, and non-polar solvents can be employed in solution polymerizations, with the latter type being more common in industrial practice. Examples of non-polar solvents include various $C_5$-$C_{12}$ cyclic and acyclic alkanes as well as their alkylated derivatives, certain liquid aromatic compounds, and mixtures thereof. The ordinarily skilled artisan is aware of other useful solvent options and combinations.

Depending on the nature of the polymer desired, the particular conditions of the solution polymerization can vary significantly. The following description is of an anionic polymerization, although cationic polymerizations also are possible. After these descriptions, optional functionalization and processing of polymers so made are discussed.

Anionic polymerization typically involves an initiator as opposed to, e.g., a catalyst. Exemplary initiators include organolithium compounds, particularly alkyllithium compounds. Examples of organolithium initiators include N-lithio-hexamethyleneimine; n-butyllithium; tributyltin lithium; dialkylaminolithium compounds such as dimethylaminolithium, diethylaminolithium, dipropylaminolithium, dibutylaminolithium and the like; dialkylaminoalkyllithium compounds such as diethylaminopropyllithium; and those trialkylstanyl lithium compounds involving $C_1$-$C_{12}$, preferably $C_1$-$C_4$, alkyl groups.

Multifunctional initiators, i.e., initiators capable of forming polymers with more than one living end, also can be used. Examples of multifunctional initiators include, but are not limited to, 1,4-dilithiobutane, 1,10-dilithiodecane, 1,20-dilithioeicosane, 1,4-dilithiobenzene, 1,4-dilithionaphthalene, 1,10-dilithioanthracene, 1,2-dilithio-1,2-diphenylethane, 1,3,5-trilithiopentane, 1,5,15-trilithioeicosane, 1,3,5-trilithiocyclohexane, 1,3,5,8-tetralithiodecane, 1,5,10,20-tetralithioeicosane, 1,2,4,6-tetralithiocyclohexane, and 4,4'-dilithiobiphenyl.

In addition to organolithium initiators, so-called functionalized initiators also can be useful. These become incorporated into the polymer chain, thus providing a functional group at the initiated end of the chain. Examples of such materials include lithiated aryl thioacetals (see, e.g., U.S. Pat. No. 7,153,919); the reaction products of organolithium compounds and, for example, N-containing organic compounds such as substituted aldimines, ketimines, secondary amines, etc., optionally pre-reacted with a compound such as diisopropenyl benzene (see, e.g., U.S. Pat. Nos. 5,153,159 and 5,567,815); and hydroxyaryl-containing initiators such as those described in U.S. Pat. Publ. No. 2010/0286348.

Formula IV compounds also can be used as initiators. Such compounds can be provided by reacting a formula I compound with a hydrocarbyl alkali metal compound such as, particularly, an organolithium compound of the type described previously. In the formula I compound (and, accordingly, also in formula IV initiators), m can be an integer of from 1 to 5 inclusive. In certain embodiments, two $OG_p$ moieties can be present, optionally bonded to adjacent ring C atoms, e.g., at the 3 and 4 positions, of the phenyl group of a formula IV initiator. As mentioned previously, M in formula IV initiators can be an alkali metal atom, preferably a K, Na or Li atom, most preferably a Li atom.

When a formula IV initiator initiates polymerization, its radical forms one end of a polymer chain. The $G_p$ moieties of this radical subsequently can be hydrolyzed so as to provide hydroxyl substituents. The identity and treatment of Gp moieties of the $OG_p$ functionalities in a formula IV initiator are the same as those discussed above in connection with monomeric B units.

A formula IV-type initiator can be made external to the polymerization vessel where it is to act as an initiator, in which case a blend of monomer(s) and solvent can be charged to the reaction vessel, followed by addition of initiator which often is added as part of a solution or blend (i.e., in a solvent carrier). For reasons of convenience, the formula IV-type often is synthesized in situ, described in detail below.

Although the ordinarily skilled artisan understands the conditions typically employed in solution polymerization, a representative description is provided for ease of reference. The following is based on a batch process, although the ordinarily skilled artisan can adapt this description to, semi-batch, continuous, or other processes.

Solution polymerization typically begins by charging a blend of monomer(s) and solvent to a suitable reaction vessel, followed by addition of a coordinator (if used) and initiator, which often are added as part of a solution or blend; alternatively, monomer(s) and coordinator can be added to the initiator. Both randomization and vinyl content (i.e., 1,2-microstructure) can be increased by including a coordinator, usually a polar compound. Up to 90 or more equivalents of coordinator can be used per equivalent of initiator, with the amount depending on, for example, the amount of vinyl content desired, the level of non-polyene monomer employed, the reaction temperature, and nature of the specific coordinator employed. Compounds useful as coordinators include organic compounds that include a heteroatom having a non-bonded pair of electrons (e.g., O or N). Examples include dialkyl ethers of mono- and oligo-alkylene glycols; crown ethers; tertiary amines such as tetramethylethylene diamine; THF; THF oligomers; linear and cyclic oligomeric oxolanyl alkanes (see, e.g., U.S. Pat. No. 4,429,091) such as 2,2'-di(tetrahydrofuryl) propane, di-piperidyl ethane, hexamethylphosphoramide, N,N'-dimethylpiperazine, diazabicyclooctane, diethyl ether, tributylamine, and the like.

Typically, a solution of polymerization solvent(s) and the monomer(s) is provided at a temperature of from about −80° to +100° C., more commonly from about −40° to +50° C., and typically from ~0° to +30° C. To this solution is added an initiating compound or, where a functionalizing unit is to be provided from the initiator, and the formula IV initiator (or a formula I precursor with an organolithium, typically an alkyllithium). The solution can have a temperature of from about −70° to ~150° C., more commonly from about −20° to ~120° C., and typically from ~10° to ~100° C. The polymerization is allowed to proceed under anhydrous, anaerobic conditions for a period of time sufficient to result in the formation of the desired polymer, usually from ~0.01 to ~100 hours, more commonly from ~0.08 to ~48 hours, and typically from ~0.15 to ~2 hours.

After a desired degree of conversion has been reached, the heat source (if used) can be removed and, if the reaction vessel is to be reserved solely for polymerizations, the reaction mixture removed to a post-polymerization vessel for functionalization and/or quenching. Regardless of how processed, this reaction mixture commonly is referred to as a "polymer cement" because of its relatively high concentration of polymer. Polymers made according to anionic techniques generally have a number average molecular weight ($M_n$) of up to ~500,000 Daltons. In certain embodiments, the $M_n$ can be as low as ~2000 Daltons; in these and/or other embodiments, the $M_n$ advantageously can be at least ~10,000 Daltons or can range from ~50,000 to ~250,000 Daltons or from ~75,000 to ~150,000 Daltons. Often, the $M_n$ is such that a quenched sample exhibits a gum Mooney viscosity ($ML_4/100°$ C.) of from ~2 to ~150, more commonly from ~2.5 to ~125, even more commonly from ~5 to ~100, and most commonly from ~10 to ~75.

Where a polymer cement is maintained in such a way so as to preserve at least some polymers with living ends, a formula IIIa-type polymer can be provided prior to quenching, advantageously when it is in the above-described polymer cement state, by introducing to the polymer cement one or more formula I compounds and allowing such compound(s) to react at a terminus of a reactive polymer chain. This type of compound hereinafter is referred to as a terminating compound. A preferred group of terminating compounds includes those with at least two $OG_p$ substituents on the phenyl ring.

Reaction of formula I compounds with a terminally active polymer can be performed relatively quickly (a few minutes to a few hours) at moderate temperatures (e.g., 0° to 75° C.). The amount of such compounds added to and reacted with the polymers can vary widely, depending significantly on the degree of desired effect, the amount of non-conventional filler(s) employed, the ratio of conventional-to-non-conventional filler particles, and the like. Based on the amount of reactive polymer chains (generally determined based on the equivalents of initiator or catalyst), the amount of formula I-type compound(s) can range from ~1:4 to ~5:4, generally from ~1:3 to ~9:8, and typically from ~1:2 to ~1:1. Lesser amounts can be employed in certain embodiments so as to preserve some reactive polymer terminals for reaction with other functionalizing agents, which can be added before, after, or with the compounds just discussed; this type of multiple functionalization can be done in place of or in addition to the types of functional initiation discussed previously. Reaction of this living polymer with any of a variety of quenching agents (discussed below) results in Z (from formula III) being a hydrogen atom while reaction with a terminating compound results in Z being the radical (defined above) of that compound.

While a polymer remains living, it can be further functionalized by reaction with a compound that includes one or more heteroatoms, i.e., a terminating compound, coupling agent and/or linking agent. The ordinarily skilled artisan is familiar with numerous examples of terminal functionalities that can be provided through this type of post-polymerization functionalization. For additional details, the interested reader is directed to any of U.S. Pat. Nos. 3,109,871, 4,015,061, 4,616,069, 4,647,625, 4,677,153, 4,935,471, 5,109,907, 5,153,159, 5,149,457, 5,196,138, 5,329,005, 5,496,940, 5,502,131, 5,567,815, 5,610,227, 5,663,398, 5,786,441, 6,812,295, 6,977,281, 7,153,919, 7,816,483, etc., as well as references cited in these patents and later publications citing these patents; see also U.S. Patent Publ. Nos. 2007/0149744, 2007/0078232, 2008/0027171, and the like. Specific exemplary terminating compounds include $SnCl_4$, $R^2_3SnCl$, $R^2_2SnCl_2$, $R^2SnCl_3$, carbodiimides, N-cyclic amides, N,N'-disubstituted cyclic ureas, cyclic amides, cyclic ureas, isocyanates, Schiff bases, 4,4'-bis(diethylamino) benzophenone, alkyl thiothiazolines, alkoxysilanes (e.g., $Si(OR^2)_4$, $R^2Si(OR^2)_3$, $R^2_2Si(OR^2)_2$, etc.) cyclic siloxanes and mixtures thereof. (In the foregoing, each $R^2$ independently is a $C_1$-$C_{20}$ alkyl group, $C_3$-$C_{20}$ cycloalkyl group, $C_6$-$C_{20}$ aryl group, or $C_7$-$C_{20}$ aralkyl group.) Specific examples of preferred terminating compounds include $SnCl_4$, tributyl tin chloride, dibutyl tin dichloride, 1,3-dimethyl-2-imidazolidinone (DMI), and 3-bis(trimethylsilyl)aminopropyl-methyldiethoxysilane.

Terminal functionality, if desired, can be provided to the living polymer while it remains in the polymerization vessel or, if desired, the polymer cement can be transferred to another vessel prior to reaction.

At this point, the resulting polymer includes one or more types of polyene mer and at least one functionalizing unit which includes an α-methylstyrene group having at least one $OG_p$ substituent bonded to its phenyl ring. The functionalizing unit(s) can be derived from the initiating compound, the monomer(s), or terminating compound. In certain aspects, more than one of the functionalizing units can be incorporated, and these can result from multiple mer, from an initiator plus one or more mer, a terminal functionality plus one or more mer, or from an initiator plus a terminal functionality.

The particular form of the substituent(s) bonded to the phenyl ring depends on the origin of the unit of which it is a part: units derived from an initiator and/or monomers will have $OG_p$ substituents while units derived from a terminating compound can have either type ($OG_p$ or OH). Ensuring that most, preferably all, $G_p$ moieties are converted to H atoms typically can be desirable so as to promote maximum interactivity with filler particles (when the polymer is used as part of a rubber composition). The processing steps (including quenching) described below can be sufficient to hydrolyze at least some of the $G_p$ moieties, thereby providing one or more hydroxyl substituents to one or more aryl groups within polymer. Alternatively, a separate reaction step designed to promote extensive, preferably complete, hydrolysis can be employed; from the exemplary technique employed in several of the examples below, the ordinarily skilled artisan can envision other potentially effective reactions. Further, the ordinarily skilled artisan understands that $OG_p$ or OH groups, regardless of location in the polymer chain, may undergo further reaction during this processing and/or compounding with one or more types of particulate fillers (described below).

Quenching, if desired, can be conducted by stirring the polymer and an active hydrogen-containing compound, such as an alcohol, water or an acid, for up to about 120 minutes at temperatures of from about 25° to about 150° C.

Solvent can be removed from the (quenched) polymer cement by conventional techniques such as drum drying, extruder drying, vacuum drying or the like, which may be combined with coagulation with water, alcohol or steam, thermal desolventization. If coagulation is performed, oven drying may be desirable.

Polymers such as those described above can display particularly advantageous properties when compounded with, inter alia, reinforcing fillers such as carbon black and silica. They can be utilized in a tread stock compound or can be blended with any conventionally employed tread stock rubber including natural rubber and/or non-functionalized synthetic rubbers such as, e.g., one or more of homo- and interpolymers that include just polyene-derived mer units (e.g., poly(butadiene), poly(isoprene), and copolymers incorporating butadiene, isoprene, and the like), SBR, butyl rubber, neoprene, ethylene/propylene rubber, ethylene/propylene/diene rubber, acrylonitrile/butadiene rubber, silicone rubber, fluoroelastomers, ethylene/acrylic rubber, ethylene/vinyl acetate interpolymer, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from about 5 to about 99% of the total rubber, with the conventional rubber(s) making up the balance of the total rubber. The minimum amount depends to a significant extent on the degree of hysteresis reduction desired.

Elastomeric compounds typically are filled to a volume fraction, which is the total volume of filler(s) added divided by the total volume of the elastomeric stock, often ~25%; typical (combined) amounts of reinforcing fillers range from ~30 to ~100 phr, with the upper end of the range being defined largely by how effectively processing equipment can handle the increased viscosities imparted when such fillers are employed.

Useful fillers include various forms of carbon black including, but not limited to, furnace black, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semi-reinforcing furnace blacks, medium processing channel blacks, hard processing channel blacks, conducting channel blacks, and acetylene blacks; mixtures of two or more of these can be used. Carbon blacks having a surface area (EMSA) of at least 20 m$^2$/g, preferably at least ~35 m$^2$/g, are preferred; see ASTM D-1765 for methods of determining surface areas of carbon blacks. The carbon blacks may be in pelletized form or an unpelletized flocculent mass, although unpelletized carbon black can be preferred for use in certain mixers.

The amount of carbon black can be up to about 50 phr, with about 5 to about 40 phr being typical.

Amorphous silica ($SiO_2$) also can be utilized as a filler. Silicas are generally classified as wet-process, hydrated silicas because they are produced by a chemical reaction in water, from which they are precipitated as ultrafine, spherical particles. These primary particles strongly associate into aggregates, which in turn combine less strongly into agglomerates. "Highly dispersible silica" is any silica having a very substantial ability to de-agglomerate and to disperse in an elastomeric matrix, which can be observed by thin section microscopy.

Surface area gives a reliable measure of the reinforcing character of different silicas; the Brunauer, Emmet and Teller ("BET") method (described in *J. Am. Chem. Soc.*, vol. 60, p. 309 et seq.) is a recognized method for determining surface area. BET surface areas of silicas generally are less than 450 m$^2$/g, commonly from ~32 to ~400 m$^2$/g or from ~100 to ~250 m$^2$/g or from ~150 to ~220 m$^2$/g.

The pH of the silica filler (when used) is generally from about 5 to about 7 or slightly over, preferably from about 5.5 to about 6.8.

Commercially available silicas include various grades of Hi-Sil™ powdered and granular silicas (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J. M. Huber Corp. (Edison, N.J.).

When silica is employed, a coupling agent such as a silane often is added so as to ensure good mixing in, and interaction with, the elastomer(s). Generally, the amount of silane that is added ranges between ~4 and ~20%, based on the weight of silica filler present in the elastomeric compound. Coupling agents can have a general formula of A-T-G, in which A represents a functional group capable of bonding physically and/or chemically with a group on the surface of the silica filler (e.g., surface silanol groups); T represents a hydrocarbon group linkage; and G represents a functional group capable of bonding with the elastomer (e.g., via a sulfur-containing linkage). Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes bearing the G and A functionalities mentioned above. Addition of a processing aid can be used to reduce the amount of silane employed. See, e.g., U.S. Pat. No. 6,525,118 for a description of fatty acid esters of sugars used as processing aids. Additional fillers useful as processing aids include, but are not limited to, mineral fillers, such as clay (hydrous aluminum silicate), talc (hydrous magnesium silicate), and mica as well as non-mineral fillers such as urea and sodium sulfate. Exemplary micas contain principally alumina, silica and potash, although other variants can be used. Additional fillers can be utilized in an amount of up to ~40 phr, typically up to ~20 phr.

Silica commonly is employed in amounts up to ~100 phr, typically in an amount from ~5 to ~80 phr. When carbon black also is present, the amount of silica can be decreased to as low as ~1 phr; as the amount of silica decreases, lesser amounts of the processing aids, plus silane if any, can be employed.

One or more non-conventional fillers having relatively high interfacial free energies, i.e., surface free energy in water values ($\gamma_{pl}$) preferably are used in conjunction with or in place of carbon black and/or silica. The term "relatively high" can be defined or characterized in a variety of ways such as, e.g., greater than that of the water-air interface, preferably several multiples (e.g., at least 2×, at least 3× or even at least 4×) of this value; at least several multiples (e.g., at least 2×, at least 3×, at least 4×, at least 5×, at least 6×, at least 7×, at least 8×, at least 9× or even at least 10×) of the $\gamma_{pl}$ value for amorphous silica; in absolute terms such as, e.g., at least ~300, at least ~400, at least ~500, at least ~600, at least ~700, at least ~750, at least ~1000, at least ~1500, and at least ~2000 mJ/m$^2$; in ranges such as, e.g., from ~300 to ~5000 mJ/m$^2$, from ~350 to ~4000 mJ/m$^2$, from ~400 to ~5000 mJ/m$^2$, from ~450 to ~4000 mJ/m$^2$, from ~500 to ~5000 mJ/m$^2$, and various sub-ranges within the foregoing and/or other combinations of high and low values; and the like.

Non-limiting examples of naturally occurring materials with relatively high interfacial free energies include F-apatite, goethite, hematite, zincite, tenorite, gibbsite, quartz, kaolinite, all forms of pyrite, and the like. Certain synthetic complex oxides also can exhibit this type of high interfacial free energy.

The foregoing types of materials typically are more dense than either carbon black or amorphous silica; thus, replacing a particular mass of carbon black or silica with an equal mass of a non-conventional filler typically will result in a much smaller volume of overall filler being present in a given compound. Accordingly, replacement typically is made on an equal volume, as opposed to equal weight, basis.

Generally, ~5 to ~60% of the conventional particulate filler material(s) can be replaced with an approximately equivalent (~0.8× to ~1.2×) volume of non-conventional filler particles. In certain embodiments, replacing ~10 to ~58% of the conventional particulate filler material(s) with an approximately equivalent (~0.85× to ~1.15×) volume of other filler particles is sufficient; in other embodiments, replacing ~15 to ~55% of the conventional particulate filler material(s) with an approximately equivalent (~0.9× to ~1.1×) volume of other filler particles is adequate; in still other embodiments, replacing ~18 to ~53% of the conventional particulate filler material(s) with an approximately equivalent (~0.95× to ~1.05×) volume of other filler particles can be preferable.

The weight inequality issue might be able to be overcome or ameliorated by employing non-standard particles. For example, one can envision essentially hollow particles of one or more types of non-conventional fillers as well as relatively light particles coated so as to have a surface that includes one or more of types of non-conventional filler compounds.

The non-conventional filler particles generally can be of approximately the same size as the conventional fillers employed in compounds. In other words, neither extremely large particles such as those employed in the aforementioned U.S. Pat. No. 5,066,702 nor extremely small particles such as those employed in the aforementioned U.S. Pat. No. 6,972,307 are required. In general, relatively small particles are preferred both for reinforcement purposes and to ensure a large number of particles are available at the tread surface.

Other conventional rubber additives also can be added. These include, for example, process oils, plasticizers, antidegradants such as antioxidants and antiozonants, curing agents and the like.

All ingredients can be mixed with standard equipment such as, e.g., Banbury or Brabender mixers. Typically, mixing occurs in two or more stages. During the first stage (often referred to as the masterbatch stage), mixing typically is begun at temperatures of ~120° to ~130° C. and increases until a so-called drop temperature, typically ~165° C., is reached.

Where a formulation includes fillers other than or in addition to carbon black, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with about 0.2 to about 5 phr of one or more known vulcanizing agents such as, for example, sulfur or peroxide-based curing systems. For a general disclosure of suitable vulcanizing agents, the interested reader is directed to an overview such as that provided in Kirk-Othmer, *Encyclopedia of Chem. Tech.*, 3d ed., (Wiley Interscience, New York, 1982), vol. 20, pp. 365-468. Vulcanizing agents, accelerators, etc., are added at a final mixing stage. To reduce the chances of undesirable scorching and/or premature onset of vulcanization, this mixing step often is done at lower temperatures, e.g., starting at ~60° to ~65° C. and not going higher than ~105° to ~110° C.

Subsequently, the compounded mixture is processed (e.g., milled) into sheets prior to being formed into any of a variety of components and then vulcanized, which typically occurs at ~5° to ~15° C. higher than the highest temperatures employed during the mixing stages, most commonly about 170° C.

Certain tests have come to be recognized as correlating certain physical properties of vulcanizates with performance of products, particularly tire treads, made therefrom. For example, reductions in hysteresis (heat build-up during operation) have been found to correlate with higher rebound values and lower loss tangent values (tan δ) at high temperature, better handling performance often correlates with higher elastic modulus values at high temperature and strain, ice traction has been found to correlate with lower modulus values at low temperatures, etc. (In the foregoing, "high temperature" typically is considered to be ~50°-65° C. while "low temperature" is considered to be ~0° to −25° C.)

Many desirable properties of vulcanizates (as well as enhanced processability of the rubber compositions from which they are prepared) are achieved when filler particles are well dispersed and exhibit excellent interactivity with the constituent polymers. The section of the polymer chain from the site of the last crosslink to an end of the polymer chain is a major source of hysteretic losses; this free end is not tied to the macromolecular network and thus cannot be involved in an efficient elastic recovery process and, as a result, energy transmitted to this section of the polymer (and vulcanizate in which such polymer is incorporated) is lost as heat. Ensuring that these polymer chain ends are tied to, or otherwise interact well with, reinforcing particulate fillers is important to many vulcanizate physical properties including reduced hysteresis.

The following non-limiting, illustrative examples provide the reader with detailed conditions and materials that can be useful in the practice of the present invention.

EXAMPLES

In the examples, dried glass vessels previously sealed with extracted septum liners and perforated crown caps under a positive N$_2$ purge were used for all preparations. Butadiene solutions (in hexane), styrene (34.5% by wt. in hexane), hexane, n-butyllithium (1.68 M in hexane), 2,2-bis (2'-tetrahydrofuryl)propane solution (1.6 M solution in hexane, stored over CaH$_2$), and 2,6-di-tert-butyl-4-methylphenol (BHT) solution in hexane were used.

from Sigma-Aldrich Co. (St. Louis, Mo.)—triethylamine (99.5%), 3,4-dihydroxybenzaldehyde(3,4-DOBA, 97%), 3,5-dihydroxybenzaldehyde (3,5-DOBA, 98%), 3',5'-dihydroxyacetophenone (3',5'-DOAP, 97%), methyltriphenylphosphonium bromide (98%), and 4-di(methylamino)pyridine (DMAP, 99%); and from ACROS Organics (Geel, Belgium)—tert-butyldimethylsilyl chloride (98%) and tetrabutylammonium fluoride (TBAF, 1.0 M in THF containing ~5% water).

Examples 1-3

Synthesis of Ketones and Aldehydes

To a dry flask under nitrogen was added ~10.00 g 3',5'-DOAP and 0.32 g DMAP, followed by ~180 mL DMF to provide a pale yellow solution. After 20.2 mL triethylamine was added, a solution of ~20.2 mL tert-butyldimethylsilyl chloride (3.0 M in THF) was added dropwise. The resulting suspension was stirred for ~1 hour at room temperature before ~150 mL hexane and ~50 mL of a saturated aqueous solution of NH$_4$Cl were added. The organic phase was washed three times with ~50 mL brine. After volatiles were removed from the organic phase, a light brown oil was obtained. This oil was purified by silica gel column chromatography (230-400 mesh from Fisher Scientific) with hexane/ethyl acetate (95:5, v/v) as eluent. After solvent was removed, a colorless oil was obtained (98% yield). Proton and $^{13}$C NMR spectroscopic analysis (Varian™ 300 MHz spectrophotometer) confirmed the product as 3',5'-bis(tert-butyldimethylsilyloxy)acetophenone [3',5'-(TBDMSO)AP, Example 1].

Similar procedures were used to make 3,4-bis(tert-butyldimethylsilyloxy)-benzaldehyde[3,4-(TBDMSO)BA, Example 2] (98%, off-white solid) from 3,4-DOBA and 3,5-bis(tert-butyldimethylsilyloxy)benzaldehyde [3,5-(TBDMSO)BA, Example 3] (90%, colorless oil) from 3,5-DOBA.

The structures of these compounds are provided below in Table 1.

Example 4

Synthesis of α-methylstyrene

To 25.4 g methyltriphenylphosphonium bromide in 130 mL THF was added 41.9 mL 1.6 M n-butyllithium solution at 0° C., which resulted in formation of an orange suspension. After ~20 minutes, 22.5 g 3',5'-(TBDMSO)AP (from Example 1) in 100 mL THF was slowly added to the suspension via cannula, resulting in formation of a yellow suspension which was stirred overnight at room temperature.

After solid was filtered out and solvent removed, raw product was purified by silica gel column chromatography with hexane/ethyl acetate (95:5, v/v), yielding 18.0 g colorless oil (80.5% yield). Proton and $^{13}$C NMR spectroscopic analysis confirmed the product as 3,5-bis(tert-butyldimethylsilyloxy)-α-methylstyrene [3,5-(TBDMSO)AMS].

Example 5 (control)

Styrene/Butadiene Copolymer

To a N$_2$-purged reactor equipped with a stirrer was added 1.57 kg hexane, 0.39 kg styrene solution, and 2.52 kg butadiene solution (21.6 wt. % in hexane). The reactor was charged with 3.37 mL n-butyllithium solution, followed by 1.24 mL 2,2-bis(2'-tetrahydrofuryl)propane solution. The reactor jacket was heated to 50° C., and the polymerization was allowed to proceed for ~75 minutes. After the polymer cement was cooled to room temperature, it was dropped into isopropanol containing BHT and drum dried. Properties of this unmodified control polymer (Example 5) are summarized below in Table 2.

Examples 6-7

Styrene/Butadiene Copolymers—Functional Initiator

To another N$_2$-purged reactor equipped with a stirrer was added 1.53 kg hexane, 0.37 kg styrene solution, and 2.32 kg butadiene solution (22.1% by wt. in hexane). The reactor was charged with a separately prepared initiator solution, which included 3.17 mL of n-butyllithium in hexane, 5.06 mL of a 1.0 M solution of 3,5-(TBDMSO)AMS (from Example 4) in hexane and 1.17 mL 2,2-bis(2'-tetrahydrofuryl)propane solution. The reactor jacket was heated to 50° C., and the polymerization was allowed to proceed for ~75

TABLE 1

| Example 1 | Example 2 | Example 3 |
|---|---|---|
| 3',5'-(TBDMSO)AP | 3,4-(TBDMSO)BA | 3,5-(TBDMSO)BA | minutes. After the polymer cement was cooled to room temperature, portions were dropped into dried bottles and treated as follows:

Example 6 terminated with isopropanol, and

Example 7 addition of isopropanol followed by addition of TBAF solution (~5:2 molar ratio relative to initiator) to hydrolyze protecting groups.

Each of these sample bottles was rotated in a 25° C. bath for ~2 hours before each cement was coagulated with isopropanol containing BHT and drum dried. The properties of these functionalized polymers are provided below in Table 2.

Other bottles containing portions of this same polymer cement were used in Examples 8-11 which follow.

Examples 8-11

Styrene/Butadiene Copolymers—Head and Tail Functionalization

To two bottles containing portions of the polymer cement prepared in Examples 6-7 were added 1.0 M 3,5-(TB-DMSO)AMS (from Example 4) in hexane. In one (designated Example 8 below), sufficient 3,5-(TBDMSO)AMS was added so as to provide an ~1:1 ratio of α-methylstyrene to lithium ions while, in another (designated Example 9 below), sufficient 3,5-(TBDMSO)AMS was added so as to provide an ~3:1 ratio of α-methylstyreneto lithium ions. The results of these additions are one polymer including one terminal (tail) functional unit (Example 8), and another including three terminal functional units (Example 9).

To another bottle containing a portion of the polymer cement prepared in Examples 6-7 was added sufficient 1.0 M 3,5-(TBDMSO)BA (from Example 3) in hexane so as to provide an ~1:1 ratio of benzaldehyde compound to lithium ions. This is designated Example 10 below.

To yet another bottle containing a portion of the polymer cement prepared in Examples 6-7 was added sufficient 1.0 M 3,4-(TBDMSO)BA (from Example 2) in hexane so as to provide an ~1:1 ratio of benzaldehyde compound to lithium ions. This is designated Example 11 below.

Each of these bottles was agitated for ~30 minutes at 50° C. Sufficient TBAF solution to de-protect the calculated amount of $OG_p$ moieties present in the respective polymers was added to each bottle, followed by tumbling for ~120 minutes in a 25° C. water bath. Each cement was coagulated with isopropanol containing BHT and drum dried. The properties of all polymers are provided below in Table 2.

Cold flow testing was performed using a Scott™ tester. Samples were prepared by melt pressing 2.5 g of polymer at 100° C. for 20 minutes in a mold using a preheated press. The resulting cylindrical samples, which had a uniform thickness of ~12 mm, were allowed to cool to room temperature before being removed from the mold. Samples were placed individually under the weight of a 5 kg calibrated weight. Sample thicknesses were recorded as a function of time for ~30 minutes, measured from time that the weight was released, with the values in the following table being thicknesses at the conclusion of the tests.

TABLE 2

| Polymer properties | | | | | | | |
|---|---|---|---|---|---|---|---|
| | 5 | 6 | 7 | 8 | 9 | 10 | 11 |
| $M_n$ (kg/mol) | 92 | 125 | 127 | 126 | 126 | 138 | 131 |
| $M_w/M_n$ | 1.04 | 1.05 | 1.08 | 1.05 | 1.05 | 1.15 | 1.10 |
| $M_p$ (kg/mol) | 96 | 127 | 128 | 129 | 130 | 129 | 129 |
| $T_g$ (° C.) | −41.1 | −35.2 | −36.7 | −35.7 | −35.8 | −35.3 | −35.9 |
| coupling (%) | 1.4 | 4.5 | 6.1 | 3.8 | 2.6 | 18.8 | 10.0 |
| Total styrene (%) | 16.6 | 20.2 | 20.2 | 20.2 | 20.2 | 20.2 | 20.2 |
| 1,2-microstructure (%) | 55.2 | 56.5 | 56.5 | 56.5 | 56.5 | 56.5 | 56.5 |
| Cold flow (mm) | 1.62 | 2.36 | 3.86 | 4.85 | 7.28 | 9.19 | 8.00 |

Examples 12-23

Filled Compositions

Vulcanizable elastomeric compounds containing reinforcing fillers were made from the polymers of Examples 5 and 7-11. Those made according to the formulation shown in Table 3a (which employs only carbon black as a particulate filler) are designated Examples 12-17, respectively, while those made according to the formulation shown in Table 3b (which employs only silica as a particulate filler) are designated Examples 18-23, respectively.

In these tables, N-phenyl-N'-(1,3-dimethylbutyl)-p-phenyldiamine acts as an antioxidant while 2,2'-dithiobisbenzothiazole, N-t-butylbenzothiazole-2-sulfenamide, and N,N'-diphenylguanidine act as accelerators.

TABLE 3a

| Compound formulation, carbon black filler | |
|---|---|
| | Amount (phr) |
| Masterbatch | |
| polymer | 100 |
| carbon black (N343 type) | 50 |
| wax | 2 |
| N-phenyl-N'-(1,3-dimethylbutyl)-p-phenylenediamine | 0.95 |
| stearic acid | 2 |
| processing oil (low PCA content) | 10 |
| Final | |
| sulfur | 1.5 |
| N-cyclohexylbenzothiazole-2-sulfenamide | 0.5 |
| N,N'-diphenylguanidine | 0.3 |
| 2,2'-dithiobisbenzothiazole | 0.5 |
| ZnO | 2.5 |
| TOTAL | 170.25 |

TABLE 3b

Compound formulation, silica filler

| Masterbatch | Amount (phr) |
|---|---|
| synthesized polymer | 80 |
| poly(isoprene) (natural rubber) | 20 |
| silica | 52.5 |
| wax | 2 |
| N-phenyl-N'-(1,3-dimethylbutyl)-p-phenyldiamine | 0.95 |
| stearic acid | 2 |
| processing oil (low PCA content) | 10 |
| Re-mill | |
| silica | 2.5 |
| silane | 5 |
| Final | |
| sulfur | 1.5 |
| ZnO | 2.5 |
| 2,2'-dithiobisbenzothiazole | 2.0 |
| N-t-butylbenzothiazole-2-sulfenamide | 0.7 |
| N,N'-diphenylguanidine | 1.4 |
| TOTAL | 183.05 |

Examples 24-35

Preparation and Testing of Vulcanizates

The compounds of Examples 12-23 were cured for ~15 minutes at 171° C. to provide vulcanizates 24-29 (carbon black) and 30-35 (silica), respectively. Results of physical testing on vulcanizates are summarized below in Tables 4 and 5.

For the "Temp. sweep" lines of these tables, the top row of data are from measurements at 0° C. while the bottom row are from measurements at 60° C.

Data corresponding to "60° C. Dynastat tan δ" were acquired from tests conducted on a Dynastat™ mechanical spectrometer (Dynastatics Instruments Corp.; Albany, N.Y.) using the following conditions: 1 Hz, 2 kg static mass and 1.25 kg dynamic load, a cylindrical (9.5 mm diameter×16 mm height) vulcanized rubber sample, and 60° C.

Data corresponding to "Bound rubber" were determined using the procedure described by J. J. Brennan et al., *Rubber Chem. and Tech.*, 40, 817 (1967).

Mooney viscosity ($ML_{1+4}$) values were determined with an Alpha Technologies™ Mooney viscometer (large rotor) using a one-minute warm-up time and a four-minute running time; tensile mechanical properties were determined using the standard procedure described in ASTM-D412; Payne effect ($\Delta G'$, i.e., the difference between G' at 0.25% strain and at 14% strain) and hysteresis (tan δ) data were obtained from dynamic experiments conducted at 60° C. and 10 Hz (strain sweep) and 2% strain and 10 Hz (temperature sweep). With respect to tensile properties, $M_x$ is modulus at x% elongation, $T_b$ is tensile strength at break, and $E_b$ is percent elongation at break.

TABLE 4

Compound and vulcanizate properties, Examples 24-29 (carbon black)

| | 24 | 25 | 26 | 27 | 28 | 29 |
|---|---|---|---|---|---|---|
| synthetic polymer (example no.) | 5 | 7 | 8 | 9 | 10 | 11 |
| Bound rubber (%) | 8.7 | 22.0 | 24.7 | 26.9 | 40.9 | 74.8 |
| Compound $ML_{1+4}$ @ 130° C. (final) | 13.6 | 33.7 | 39.8 | 50.8 | 95.9 | 83.4 |
| MDR2000 @ 171° C. (final) | | | | | | |
| ML (kg · cm) | 0.70 | 1.11 | 1.18 | 1.29 | 1.94 | 1.96 |
| MH (kg · cm) | 15.77 | 19.36 | 20.15 | 20.92 | 20.19 | 18.49 |
| $t_{50}$ (min) | 2.98 | 1.65 | 1.56 | 1.31 | 1.23 | 1.17 |
| $t_{90}$ (min) | 8.91 | 8.90 | 9.84 | 10.73 | 9.57 | 9.76 |
| Dynatstat ™ tan δ @ 60° C. (final) | 0.2351 | 0.1490 | 0.1472 | 0.1212 | 0.0892 | 0.0860 |
| Tensile @ 23° C. (final, unaged) | | | | | | |
| $M_{50}$ (MPa) | 1.64 | 1.90 | 1.89 | 2.03 | 1.96 | 1.73 |
| $M_{300}$ (MPa) | 10.96 | 16.41 | 17.02 | 18.19 | 20.39 | 18.15 |
| $T_b$ (MPa) | 15.5 | 18.6 | 16.6 | 18.3 | 21.2 | 21.3 |
| $E_b$ (%) | 396 | 333 | 295 | 302 | 308 | 338 |
| Tensile @ 100° C. (final, unaged) | | | | | | |
| $M_{50}$ (MPa) | 1.23 | 1.54 | 1.63 | 1.73 | 1.73 | 1.58 |
| $M_{200}$ (MPa) | 5.28 | 8.05 | 8.33 | 8.95 | 10.22 | 8.63 |
| $T_b$ (MPa) | 7.5 | 9.1 | 9.5 | 10.7 | 9.5 | 10.1 |
| $E_b$ (%) | 265 | 219 | 217 | 228 | 191 | 222 |
| Strain sweep (60° C., 10 Hz, final) | | | | | | |
| G' @ 5% strain (MPa) | 2.91 | 2.57 | 2.40 | 2.33 | 2.35 | 2.33 |
| G" @ 5% strain (MPa) | 0.73 | 0.41 | 0.34 | 0.26 | 0.21 | 0.19 |
| tan δ @ 5% strain | 0.2513 | 0.1611 | 0.1436 | 0.1135 | 0.0892 | 0.0835 |
| $\Delta G'$ (MPa) | 4.00 | 1.67 | 1.33 | 0.83 | 0.66 | 0.58 |
| Temp. sweep (2% strain, 10 Hz, final) | | | | | | |
| G' (MPa) | 14.54 | 14.01 | 12.20 | 12.79 | 9.53 | 8.54 |
| | 5.22 | 4.98 | 4.56 | 4.99 | 3.93 | 3.69 |
| G" (MPa) | 4.99 | 5.77 | 5.12 | 5.33 | 4.19 | 3.70 |
| | 1.27 | 0.94 | 0.82 | 0.78 | 0.47 | 0.41 |

TABLE 4-continued

Compound and vulcanizate properties, Examples 24-29 (carbon black)

| | 24 | 25 | 26 | 27 | 28 | 29 |
|---|---|---|---|---|---|---|
| tan δ | 0.3426 | 0.4108 | 0.4197 | 0.4160 | 0.4387 | 0.4324 |
| | 0.2437 | 0.1888 | 0.1796 | 0.1564 | 0.1186 | 0.1103 |

TABLE 5

Compound and vulcanizate properties, Examples 30-35 (silica)

| | 30 | 31 | 32 | 33 | 34 | 35 |
|---|---|---|---|---|---|---|
| synthetic polymer (example no.) | 5 | 7 | 8 | 9 | 10 | 11 |
| Bound rubber (%) | 18.7 | 25.0 | 26.5 | 30.6 | 46.3 | 56.7 |
| Compound $ML_{1+4}$ @ 130° C. (final) | 11.9 | 25.1 | 27.9 | 34.0 | 60.9 | 68.1 |
| MDR2000 @ 171° C. (final) | | | | | | |
| ML (kg · cm) | 1.31 | 1.67 | 1.69 | 1.63 | 2.28 | 2.35 |
| MH (kg · cm) | 22.11 | 24.05 | 24.33 | 23.95 | 22.11 | 21.84 |
| $t_{50}$ (min) | 2.71 | 2.15 | 2.05 | 1.90 | 1.81 | 1.76 |
| $t_{90}$ (min) | 8.82 | 5.65 | 5.95 | 5.40 | 5.52 | 5.05 |
| Dynatstat ™ tan δ @ 60° C. (final) | 0.1460 | 0.1063 | 0.0970 | 0.0850 | 0.0600 | 0.0555 |
| Tensile @ 23° C. (final, unaged) | | | | | | |
| $M_{50}$ (MPa) | 1.97 | 2.06 | 2.09 | 2.04 | 1.85 | 1.89 |
| $M_{300}$ (MPa) | 12.02 | 14.46 | — | 15.16 | 16.76 | — |
| $T_b$ (MPa) | 13.3 | 15.4 | 13.7 | 15.9 | 16.9 | 14.9 |
| $E_b$ (%) | 324 | 315 | 279 | 309 | 301 | 273 |
| Tensile @ 100° C. (final, unaged) | | | | | | |
| $M_{50}$ (MPa) | 1.71 | 1.90 | 2.00 | 1.95 | 1.90 | 1.91 |
| $M_{100}$ (MPa) | 3.15 | 3.60 | 3.84 | 3.73 | 3.84 | 3.81 |
| $T_b$ (MPa) | 6.1 | 6.6 | 6.8 | 6.7 | 6.4 | 6.5 |
| $E_b$ (%) | 189 | 177 | 170 | 171 | 154 | 157 |
| Strain sweep (60° C., 10 Hz, final) | | | | | | |
| G' @ 5% strain (MPa) | 3.74 | 3.38 | 3.25 | 2.94 | 2.48 | 2.29 |
| G" @ 5% strain (MPa) | 0.63 | 0.43 | 0.37 | 0.29 | 0.16 | 0.13 |
| tan δ @ 5% strain | 0.1677 | 0.1259 | 0.1147 | 0.0975 | 0.0635 | 0.0579 |
| ΔG' (MPa) | 4.10 | 2.69 | 2.17 | 1.48 | 0.58 | 0.47 |
| Temp. sweep (2% strain, 10 Hz, final) | | | | | | |
| G' (MPa) | 12.25 | 12.62 | 11.53 | 11.23 | 7.34 | 7.48 |
| | 6.11 | 6.21 | 5.61 | 5.53 | 3.80 | 3.84 |
| G" (MPa) | 3.36 | 4.28 | 4.05 | 4.17 | 2.92 | 2.98 |
| | 0.91 | 0.74 | 0.65 | 0.63 | 0.28 | 0.27 |
| tan δ | 0.2746 | 0.3391 | 0.3516 | 0.3715 | 0.3975 | 0.3981 |
| | 0.1483 | 0.1185 | 0.1165 | 0.1137 | 0.0739 | 0.0710 |

The data from the foregoing tables show that hydroxyl group-containing α-methylstyrene functional SBR interpolymers exhibit excellent interaction with carbon black and silica filler as evidenced by decreases in high temperature tan δ values, reductions in ΔG', increased low temperature tan δ, and the like.

Strain sweep test results are tabulated in Tables 6a-6b (carbon black) and 6c-6d (silica), while temperature sweep tan δ test results are tabulated in Tables 7a and 7b.

TABLE 6a

Results of strain sweep testing @ 60° C., Examples 24-26

| | 24 | | | 25 | | | 26 | | |
|---|---|---|---|---|---|---|---|---|---|
| Strain (%) | G' (MPa) | G" (MPa) | tan δ | G' (MPa) | G" (MPa) | tan δ | G' (MPa) | G" (MPa) | tan δ |
| 0.24 | 6.17 | 0.743 | 0.1204 | 3.79 | 0.347 | 0.0915 | 3.34 | 0.274 | 0.0821 |
| 0.49 | 5.63 | 0.845 | 0.1500 | 3.66 | 0.364 | 0.0994 | 3.26 | 0.287 | 0.0880 |
| 0.73 | 5.14 | 0.912 | 0.1776 | 3.53 | 0.390 | 0.1106 | 3.17 | 0.304 | 0.0962 |
| 0.98 | 4.77 | 0.942 | 0.1977 | 3.41 | 0.411 | 0.1203 | 3.08 | 0.322 | 0.1046 |
| 1.23 | 4.47 | 0.950 | 0.2124 | 3.31 | 0.426 | 0.1287 | 3.00 | 0.333 | 0.1111 |
| 1.47 | 4.23 | 0.948 | 0.2240 | 3.22 | 0.436 | 0.1354 | 2.93 | 0.343 | 0.1171 |

TABLE 6a-continued

Results of strain sweep testing @ 60° C., Examples 24-26

| | 24 | | | 25 | | | 26 | | |
|---|---|---|---|---|---|---|---|---|---|
| Strain (%) | G' (MPa) | G" (MPa) | tan δ | G' (MPa) | G" (MPa) | tan δ | G' (MPa) | G" (MPa) | tan δ |
| 1.72 | 4.04 | 0.937 | 0.2320 | 3.14 | 0.442 | 0.1409 | 2.87 | 0.349 | 0.1217 |
| 1.97 | 3.88 | 0.920 | 0.2374 | 3.07 | 0.445 | 0.1452 | 2.81 | 0.353 | 0.1258 |
| 2.21 | 3.74 | 0.904 | 0.2420 | 3.00 | 0.447 | 0.1487 | 2.76 | 0.357 | 0.1295 |
| 2.46 | 3.62 | 0.888 | 0.2456 | 2.95 | 0.447 | 0.1517 | 2.71 | 0.358 | 0.1322 |
| 2.71 | 3.51 | 0.871 | 0.2481 | 2.90 | 0.446 | 0.1538 | 2.67 | 0.360 | 0.1348 |
| 2.95 | 3.42 | 0.855 | 0.2501 | 2.85 | 0.444 | 0.1558 | 2.63 | 0.360 | 0.1368 |
| 3.20 | 3.33 | 0.838 | 0.2514 | 2.80 | 0.442 | 0.1576 | 2.59 | 0.358 | 0.1383 |
| 3.44 | 3.26 | 0.821 | 0.2520 | 2.76 | 0.439 | 0.1588 | 2.56 | 0.358 | 0.1399 |
| 3.69 | 3.19 | 0.806 | 0.2527 | 2.73 | 0.435 | 0.1595 | 2.53 | 0.356 | 0.1408 |
| 3.94 | 3.13 | 0.791 | 0.2529 | 2.69 | 0.432 | 0.1603 | 2.50 | 0.355 | 0.1418 |
| 4.18 | 3.07 | 0.776 | 0.2529 | 2.66 | 0.428 | 0.1606 | 2.47 | 0.353 | 0.1425 |
| 4.43 | 3.02 | 0.761 | 0.2524 | 2.63 | 0.424 | 0.1609 | 2.45 | 0.351 | 0.1431 |
| 4.68 | 2.97 | 0.747 | 0.2518 | 2.61 | 0.420 | 0.1613 | 2.43 | 0.348 | 0.1435 |
| 4.92 | 2.92 | 0.734 | 0.2514 | 2.58 | 0.416 | 0.1612 | 2.41 | 0.346 | 0.1436 |
| 5.17 | 2.88 | 0.723 | 0.2511 | 2.56 | 0.412 | 0.1610 | 2.39 | 0.343 | 0.1436 |
| 5.41 | 2.84 | 0.710 | 0.2503 | 2.54 | 0.408 | 0.1608 | 2.37 | 0.341 | 0.1439 |
| 5.66 | 2.80 | 0.698 | 0.2491 | 2.51 | 0.405 | 0.1609 | 2.35 | 0.338 | 0.1437 |
| 5.91 | 2.77 | 0.686 | 0.2481 | 2.49 | 0.400 | 0.1602 | 2.33 | 0.335 | 0.1436 |
| 6.15 | 2.73 | 0.675 | 0.2472 | 2.48 | 0.396 | 0.1600 | 2.32 | 0.332 | 0.1434 |
| 6.64 | 2.67 | 0.655 | 0.2452 | 2.44 | 0.388 | 0.1592 | 2.29 | 0.327 | 0.1430 |
| 7.14 | 2.62 | 0.636 | 0.2432 | 2.41 | 0.381 | 0.1584 | 2.26 | 0.321 | 0.1423 |
| 7.63 | 2.57 | 0.619 | 0.2413 | 2.38 | 0.374 | 0.1571 | 2.23 | 0.316 | 0.1417 |
| 8.12 | 2.52 | 0.603 | 0.2393 | 2.35 | 0.366 | 0.1559 | 2.21 | 0.311 | 0.1409 |
| 8.61 | 2.48 | 0.588 | 0.2373 | 2.32 | 0.360 | 0.1547 | 2.19 | 0.306 | 0.1400 |
| 9.11 | 2.44 | 0.573 | 0.2354 | 2.30 | 0.354 | 0.1538 | 2.16 | 0.302 | 0.1394 |
| 9.60 | 2.40 | 0.560 | 0.2336 | 2.28 | 0.347 | 0.1525 | 2.14 | 0.296 | 0.1380 |
| 10.09 | 2.36 | 0.548 | 0.2318 | 2.26 | 0.342 | 0.1515 | 2.12 | 0.292 | 0.1374 |
| 10.58 | 2.33 | 0.536 | 0.2300 | 2.24 | 0.336 | 0.1504 | 2.11 | 0.287 | 0.1363 |
| 11.07 | 2.30 | 0.525 | 0.2285 | 2.22 | 0.331 | 0.1492 | 2.09 | 0.283 | 0.1353 |
| 11.57 | 2.27 | 0.515 | 0.2269 | 2.20 | 0.326 | 0.1485 | 2.07 | 0.279 | 0.1344 |
| 12.06 | 2.24 | 0.505 | 0.2256 | 2.18 | 0.321 | 0.1472 | 2.06 | 0.275 | 0.1336 |
| 12.55 | 2.21 | 0.495 | 0.2238 | 2.16 | 0.316 | 0.1462 | 2.05 | 0.271 | 0.1326 |
| 13.04 | 2.19 | 0.487 | 0.2226 | 2.15 | 0.312 | 0.1453 | 2.03 | 0.268 | 0.1318 |
| 14.02 | 2.14 | 0.471 | 0.2200 | 2.12 | 0.304 | 0.1435 | 2.01 | 0.261 | 0.1302 |

TABLE 6b

Results of strain sweep testing @ 60° C., Examples 27-29

| | 27 | | | 28 | | | 29 | | |
|---|---|---|---|---|---|---|---|---|---|
| Strain (%) | G' (MPa) | G" (MPa) | tan δ | G' (MPa) | G" (MPa) | tan δ | G' (MPa) | G" (MPa) | tan δ |
| 0.24 | 2.87 | 0.211 | 0.0735 | 2.76 | 0.169 | 0.0613 | 2.70 | 0.162 | 0.0602 |
| 0.49 | 2.83 | 0.216 | 0.0764 | 2.73 | 0.172 | 0.0630 | 2.67 | 0.165 | 0.0618 |
| 0.74 | 2.79 | 0.224 | 0.0805 | 2.70 | 0.181 | 0.0669 | 2.64 | 0.170 | 0.0642 |
| 0.99 | 2.75 | 0.233 | 0.0849 | 2.67 | 0.185 | 0.0694 | 2.62 | 0.176 | 0.0672 |
| 1.23 | 2.70 | 0.241 | 0.0893 | 2.64 | 0.191 | 0.0725 | 2.59 | 0.180 | 0.0696 |
| 1.48 | 2.67 | 0.248 | 0.0931 | 2.61 | 0.195 | 0.0748 | 2.56 | 0.185 | 0.0721 |
| 1.73 | 2.63 | 0.254 | 0.0964 | 2.58 | 0.200 | 0.0775 | 2.54 | 0.187 | 0.0738 |
| 1.98 | 2.60 | 0.258 | 0.0993 | 2.56 | 0.203 | 0.0795 | 2.51 | 0.190 | 0.0755 |
| 2.22 | 2.56 | 0.262 | 0.1023 | 2.53 | 0.206 | 0.0813 | 2.49 | 0.193 | 0.0774 |
| 2.47 | 2.54 | 0.264 | 0.1042 | 2.51 | 0.207 | 0.0827 | 2.47 | 0.194 | 0.0786 |
| 2.71 | 2.51 | 0.266 | 0.1060 | 2.49 | 0.209 | 0.0839 | 2.46 | 0.195 | 0.0795 |
| 2.96 | 2.49 | 0.267 | 0.1076 | 2.47 | 0.210 | 0.0850 | 2.44 | 0.197 | 0.0809 |
| 3.21 | 2.46 | 0.268 | 0.1090 | 2.45 | 0.211 | 0.0862 | 2.42 | 0.198 | 0.0816 |
| 3.45 | 2.44 | 0.268 | 0.1101 | 2.43 | 0.211 | 0.0868 | 2.41 | 0.197 | 0.0820 |
| 3.70 | 2.42 | 0.269 | 0.1111 | 2.42 | 0.211 | 0.0874 | 2.39 | 0.198 | 0.0826 |
| 3.94 | 2.40 | 0.268 | 0.1118 | 2.40 | 0.211 | 0.0879 | 2.38 | 0.197 | 0.0829 |
| 4.19 | 2.38 | 0.267 | 0.1121 | 2.39 | 0.211 | 0.0883 | 2.37 | 0.196 | 0.0830 |
| 4.44 | 2.37 | 0.267 | 0.1129 | 2.37 | 0.210 | 0.0886 | 2.36 | 0.196 | 0.0833 |
| 4.68 | 2.35 | 0.266 | 0.1131 | 2.36 | 0.210 | 0.0888 | 2.34 | 0.195 | 0.0834 |
| 4.93 | 2.34 | 0.265 | 0.1133 | 2.35 | 0.210 | 0.0892 | 2.33 | 0.195 | 0.0834 |
| 5.17 | 2.32 | 0.264 | 0.1137 | 2.34 | 0.208 | 0.0891 | 2.32 | 0.194 | 0.0836 |
| 5.42 | 2.31 | 0.263 | 0.1140 | 2.33 | 0.208 | 0.0892 | 2.31 | 0.193 | 0.0833 |
| 5.67 | 2.30 | 0.262 | 0.1140 | 2.32 | 0.206 | 0.0890 | 2.31 | 0.192 | 0.0834 |
| 5.91 | 2.28 | 0.260 | 0.1140 | 2.31 | 0.205 | 0.0891 | 2.30 | 0.191 | 0.0833 |
| 6.16 | 2.27 | 0.258 | 0.1137 | 2.30 | 0.205 | 0.0891 | 2.29 | 0.191 | 0.0833 |

TABLE 6b-continued

Results of strain sweep testing @ 60° C., Examples 27-29

| Strain (%) | 27 G' (MPa) | 27 G" (MPa) | 27 tan δ | 28 G' (MPa) | 28 G" (MPa) | 28 tan δ | 29 G' (MPa) | 29 G" (MPa) | 29 tan δ |
|---|---|---|---|---|---|---|---|---|---|
| 6.65 | 2.25 | 0.256 | 0.1137 | 2.28 | 0.202 | 0.0887 | 2.27 | 0.188 | 0.0829 |
| 7.14 | 2.23 | 0.253 | 0.1135 | 2.26 | 0.200 | 0.0885 | 2.26 | 0.187 | 0.0827 |
| 7.64 | 2.21 | 0.250 | 0.1130 | 2.25 | 0.198 | 0.0881 | 2.24 | 0.185 | 0.0822 |
| 8.13 | 2.19 | 0.247 | 0.1126 | 2.23 | 0.196 | 0.0878 | 2.23 | 0.183 | 0.0820 |
| 8.62 | 2.18 | 0.244 | 0.1122 | 2.22 | 0.194 | 0.0873 | 2.22 | 0.181 | 0.0814 |
| 9.11 | 2.16 | 0.241 | 0.1115 | 2.21 | 0.192 | 0.0868 | 2.21 | 0.179 | 0.0811 |
| 9.60 | 2.14 | 0.238 | 0.1108 | 2.20 | 0.190 | 0.0867 | 2.20 | 0.177 | 0.0806 |
| 10.09 | 2.13 | 0.235 | 0.1103 | 2.18 | 0.188 | 0.0859 | 2.19 | 0.175 | 0.0801 |
| 10.59 | 2.12 | 0.232 | 0.1098 | 2.17 | 0.186 | 0.0856 | 2.18 | 0.174 | 0.0797 |
| 11.08 | 2.10 | 0.230 | 0.1094 | 2.16 | 0.184 | 0.0850 | 2.17 | 0.172 | 0.0795 |
| 11.57 | 2.09 | 0.227 | 0.1084 | 2.15 | 0.182 | 0.0846 | 2.16 | 0.170 | 0.0789 |
| 12.06 | 2.08 | 0.224 | 0.1079 | 2.14 | 0.180 | 0.0843 | 2.15 | 0.169 | 0.0787 |
| 12.55 | 2.07 | 0.222 | 0.1074 | 2.13 | 0.179 | 0.0839 | 2.14 | 0.167 | 0.0782 |
| 13.04 | 2.06 | 0.220 | 0.1071 | 2.12 | 0.176 | 0.0832 | 2.13 | 0.166 | 0.0780 |
| 14.02 | 2.04 | 0.216 | 0.1061 | 2.10 | 0.174 | 0.0826 | 2.11 | 0.164 | 0.0775 |

TABLE 6c

Results of strain sweep testing @ 60° C., Examples 30-32

| Strain (%) | 30 G' (MPa) | 30 G" (MPa) | 30 tan δ | 31 G' (MPa) | 31 G" (MPa) | 31 tan δ | 32 G' (MPa) | 32 G" (MPa) | 32 tan δ |
|---|---|---|---|---|---|---|---|---|---|
| 0.24 | 6.72 | 0.598 | 0.0891 | 5.22 | 0.359 | 0.0687 | 4.71 | 0.302 | 0.0641 |
| 0.49 | 6.27 | 0.666 | 0.1061 | 5.01 | 0.401 | 0.0800 | 4.55 | 0.329 | 0.0723 |
| 0.74 | 5.88 | 0.706 | 0.1202 | 4.79 | 0.428 | 0.0893 | 4.39 | 0.354 | 0.0805 |
| 0.98 | 5.57 | 0.726 | 0.1303 | 4.61 | 0.443 | 0.0962 | 4.24 | 0.371 | 0.0874 |
| 1.23 | 5.33 | 0.728 | 0.1366 | 4.46 | 0.456 | 0.1023 | 4.12 | 0.385 | 0.0933 |
| 1.48 | 5.12 | 0.731 | 0.1426 | 4.32 | 0.461 | 0.1068 | 4.01 | 0.393 | 0.0979 |
| 1.72 | 4.94 | 0.725 | 0.1466 | 4.21 | 0.464 | 0.1103 | 3.92 | 0.398 | 0.1016 |
| 1.97 | 4.80 | 0.721 | 0.1504 | 4.11 | 0.464 | 0.1129 | 3.84 | 0.399 | 0.1040 |
| 2.21 | 4.66 | 0.713 | 0.1528 | 4.02 | 0.465 | 0.1157 | 3.76 | 0.400 | 0.1063 |
| 2.46 | 4.55 | 0.706 | 0.1554 | 3.94 | 0.463 | 0.1176 | 3.70 | 0.399 | 0.1080 |
| 2.70 | 4.44 | 0.700 | 0.1576 | 3.87 | 0.459 | 0.1188 | 3.64 | 0.398 | 0.1094 |
| 2.95 | 4.34 | 0.692 | 0.1595 | 3.80 | 0.457 | 0.1204 | 3.58 | 0.396 | 0.1106 |
| 3.19 | 4.25 | 0.684 | 0.1608 | 3.74 | 0.454 | 0.1214 | 3.53 | 0.395 | 0.1117 |
| 3.44 | 4.17 | 0.677 | 0.1623 | 3.68 | 0.450 | 0.1224 | 3.49 | 0.392 | 0.1126 |
| 3.69 | 4.09 | 0.670 | 0.1637 | 3.63 | 0.446 | 0.1229 | 3.44 | 0.390 | 0.1132 |
| 3.93 | 4.02 | 0.662 | 0.1647 | 3.58 | 0.443 | 0.1237 | 3.40 | 0.387 | 0.1136 |
| 4.18 | 3.95 | 0.653 | 0.1653 | 3.53 | 0.439 | 0.1243 | 3.36 | 0.383 | 0.1139 |
| 4.42 | 3.88 | 0.645 | 0.1661 | 3.48 | 0.435 | 0.1250 | 3.33 | 0.381 | 0.1144 |
| 4.67 | 3.82 | 0.638 | 0.1670 | 3.44 | 0.431 | 0.1254 | 3.29 | 0.377 | 0.1145 |
| 4.91 | 3.77 | 0.631 | 0.1675 | 3.40 | 0.428 | 0.1258 | 3.26 | 0.374 | 0.1146 |
| 5.16 | 3.71 | 0.623 | 0.1680 | 3.36 | 0.423 | 0.1261 | 3.23 | 0.371 | 0.1148 |
| 5.41 | 3.66 | 0.617 | 0.1687 | 3.32 | 0.420 | 0.1263 | 3.20 | 0.368 | 0.1151 |
| 5.65 | 3.61 | 0.610 | 0.1691 | 3.29 | 0.416 | 0.1267 | 3.17 | 0.365 | 0.1152 |
| 5.90 | 3.56 | 0.602 | 0.1690 | 3.25 | 0.412 | 0.1266 | 3.14 | 0.361 | 0.1151 |
| 6.14 | 3.51 | 0.596 | 0.1697 | 3.22 | 0.408 | 0.1267 | 3.11 | 0.358 | 0.1149 |
| 6.64 | 3.43 | 0.582 | 0.1699 | 3.15 | 0.400 | 0.1270 | 3.06 | 0.351 | 0.1148 |
| 7.13 | 3.34 | 0.569 | 0.1700 | 3.09 | 0.393 | 0.1270 | 3.01 | 0.345 | 0.1146 |
| 7.62 | 3.27 | 0.558 | 0.1706 | 3.04 | 0.386 | 0.1269 | 2.97 | 0.340 | 0.1144 |
| 8.11 | 3.20 | 0.545 | 0.1706 | 2.99 | 0.379 | 0.1270 | 2.93 | 0.334 | 0.1142 |
| 8.60 | 3.13 | 0.534 | 0.1706 | 2.94 | 0.372 | 0.1266 | 2.89 | 0.329 | 0.1140 |
| 9.09 | 3.07 | 0.523 | 0.1705 | 2.89 | 0.366 | 0.1266 | 2.85 | 0.324 | 0.1137 |
| 9.58 | 3.01 | 0.513 | 0.1704 | 2.84 | 0.359 | 0.1260 | 2.81 | 0.318 | 0.1132 |
| 10.07 | 2.95 | 0.503 | 0.1704 | 2.80 | 0.353 | 0.1258 | 2.77 | 0.313 | 0.1127 |
| 10.56 | 2.90 | 0.493 | 0.1701 | 2.76 | 0.346 | 0.1255 | 2.74 | 0.309 | 0.1126 |
| 11.06 | 2.85 | 0.484 | 0.1699 | 2.72 | 0.341 | 0.1251 | 2.71 | 0.303 | 0.1120 |
| 11.55 | 2.80 | 0.476 | 0.1699 | 2.69 | 0.335 | 0.1246 | 2.68 | 0.299 | 0.1117 |
| 12.04 | 2.75 | 0.466 | 0.1693 | 2.65 | 0.329 | 0.1242 | 2.65 | 0.295 | 0.1113 |
| 12.53 | 2.71 | 0.458 | 0.1689 | 2.62 | 0.324 | 0.1237 | 2.62 | 0.290 | 0.1107 |
| 13.02 | 2.67 | 0.450 | 0.1686 | 2.58 | 0.318 | 0.1232 | 2.59 | 0.286 | 0.1103 |
| 14.00 | 2.59 | 0.435 | 0.1679 | 2.52 | 0.309 | 0.1225 | 2.54 | 0.278 | 0.1095 |

TABLE 6d

Results of strain sweep testing @ 60° C., Examples 33-35

| | 33 | | | 34 | | | 35 | | |
|---|---|---|---|---|---|---|---|---|---|
| Strain (%) | G' (MPa) | G" (MPa) | tan δ | G' (MPa) | G" (MPa) | tan δ | G' (MPa) | G" (MPa) | tan δ |
| 0.24 | 3.87 | 0.223 | 0.0578 | 2.80 | 0.130 | 0.0464 | 2.54 | 0.114 | 0.0451 |
| 0.49 | 3.79 | 0.244 | 0.0643 | 2.78 | 0.133 | 0.0478 | 2.52 | 0.112 | 0.0444 |
| 0.74 | 3.70 | 0.259 | 0.0698 | 2.75 | 0.137 | 0.0498 | 2.51 | 0.113 | 0.0453 |
| 0.99 | 3.62 | 0.272 | 0.0751 | 2.74 | 0.142 | 0.0520 | 2.49 | 0.117 | 0.0470 |
| 1.23 | 3.55 | 0.283 | 0.0797 | 2.71 | 0.145 | 0.0533 | 2.48 | 0.121 | 0.0488 |
| 1.48 | 3.48 | 0.288 | 0.0829 | 2.69 | 0.147 | 0.0548 | 2.46 | 0.123 | 0.0499 |
| 1.73 | 3.42 | 0.293 | 0.0857 | 2.67 | 0.151 | 0.0565 | 2.44 | 0.125 | 0.0511 |
| 1.97 | 3.36 | 0.295 | 0.0879 | 2.65 | 0.152 | 0.0573 | 2.43 | 0.126 | 0.0521 |
| 2.22 | 3.31 | 0.297 | 0.0898 | 2.63 | 0.154 | 0.0586 | 2.41 | 0.128 | 0.0532 |
| 2.46 | 3.27 | 0.299 | 0.0916 | 2.62 | 0.157 | 0.0600 | 2.40 | 0.129 | 0.0538 |
| 2.71 | 3.22 | 0.299 | 0.0928 | 2.60 | 0.157 | 0.0604 | 2.39 | 0.131 | 0.0548 |
| 2.96 | 3.18 | 0.299 | 0.0938 | 2.58 | 0.158 | 0.0612 | 2.38 | 0.131 | 0.0552 |
| 3.21 | 3.15 | 0.298 | 0.0947 | 2.57 | 0.158 | 0.0617 | 2.36 | 0.132 | 0.0559 |
| 3.45 | 3.11 | 0.297 | 0.0953 | 2.55 | 0.159 | 0.0623 | 2.35 | 0.132 | 0.0562 |
| 3.69 | 3.08 | 0.295 | 0.0958 | 2.54 | 0.159 | 0.0625 | 2.34 | 0.132 | 0.0563 |
| 3.94 | 3.05 | 0.294 | 0.0963 | 2.53 | 0.159 | 0.0628 | 2.33 | 0.132 | 0.0567 |
| 4.19 | 3.02 | 0.292 | 0.0967 | 2.52 | 0.159 | 0.0631 | 2.32 | 0.133 | 0.0574 |
| 4.43 | 3.00 | 0.291 | 0.0970 | 2.50 | 0.158 | 0.0633 | 2.31 | 0.133 | 0.0574 |
| 4.68 | 2.97 | 0.289 | 0.0972 | 2.49 | 0.158 | 0.0634 | 2.30 | 0.133 | 0.0576 |
| 4.92 | 2.95 | 0.287 | 0.0974 | 2.48 | 0.158 | 0.0635 | 2.29 | 0.133 | 0.0579 |
| 5.17 | 2.92 | 0.285 | 0.0976 | 2.47 | 0.157 | 0.0634 | 2.29 | 0.133 | 0.0581 |
| 5.42 | 2.90 | 0.284 | 0.0978 | 2.46 | 0.157 | 0.0638 | 2.28 | 0.133 | 0.0583 |
| 5.66 | 2.88 | 0.282 | 0.0978 | 2.45 | 0.156 | 0.0636 | 2.27 | 0.133 | 0.0585 |
| 5.91 | 2.86 | 0.281 | 0.0981 | 2.44 | 0.156 | 0.0636 | 2.26 | 0.133 | 0.0586 |
| 6.15 | 2.84 | 0.278 | 0.0980 | 2.44 | 0.156 | 0.0639 | 2.25 | 0.132 | 0.0584 |
| 6.64 | 2.80 | 0.274 | 0.0978 | 2.42 | 0.154 | 0.0636 | 2.24 | 0.131 | 0.0585 |
| 7.14 | 2.76 | 0.271 | 0.0982 | 2.40 | 0.154 | 0.0640 | 2.22 | 0.130 | 0.0586 |
| 7.63 | 2.73 | 0.267 | 0.0980 | 2.39 | 0.152 | 0.0636 | 2.21 | 0.130 | 0.0588 |
| 8.12 | 2.70 | 0.264 | 0.0979 | 2.37 | 0.151 | 0.0636 | 2.20 | 0.129 | 0.0585 |
| 8.61 | 2.67 | 0.261 | 0.0978 | 2.36 | 0.149 | 0.0634 | 2.19 | 0.128 | 0.0585 |
| 9.10 | 2.63 | 0.257 | 0.0975 | 2.34 | 0.149 | 0.0636 | 2.17 | 0.127 | 0.0584 |
| 9.60 | 2.61 | 0.254 | 0.0973 | 2.33 | 0.147 | 0.0631 | 2.16 | 0.126 | 0.0581 |
| 10.09 | 2.58 | 0.250 | 0.0971 | 2.32 | 0.146 | 0.0630 | 2.15 | 0.125 | 0.0581 |
| 10.58 | 2.55 | 0.247 | 0.0968 | 2.30 | 0.145 | 0.0629 | 2.14 | 0.124 | 0.0579 |
| 11.07 | 2.52 | 0.244 | 0.0966 | 2.29 | 0.144 | 0.0627 | 2.13 | 0.123 | 0.0578 |
| 11.56 | 2.50 | 0.241 | 0.0962 | 2.28 | 0.143 | 0.0627 | 2.12 | 0.122 | 0.0576 |
| 12.05 | 2.48 | 0.237 | 0.0959 | 2.27 | 0.142 | 0.0625 | 2.11 | 0.121 | 0.0574 |
| 12.54 | 2.45 | 0.235 | 0.0958 | 2.25 | 0.140 | 0.0623 | 2.10 | 0.120 | 0.0573 |
| 13.03 | 2.43 | 0.232 | 0.0953 | 2.24 | 0.140 | 0.0624 | 2.09 | 0.119 | 0.0572 |
| 14.01 | 2.39 | 0.227 | 0.0951 | 2.21 | 0.137 | 0.0617 | 2.07 | 0.118 | 0.0568 |

TABLE 7a

Results (tan δ) of temperature sweep testing, Examples 24-29

| Temp. (° C.) | 24 | 25 | 26 | 27 | 28 | 29 |
|---|---|---|---|---|---|---|
| −80.1 | 0.0208 | 0.0225 | 0.0228 | 0.0232 | 0.0220 | 0.0196 |
| −76.0 | 0.0214 | 0.0214 | 0.0216 | 0.0217 | 0.0207 | 0.0189 |
| −70.0 | 0.0207 | 0.0208 | 0.0209 | 0.0207 | 0.0197 | 0.0186 |
| −66.0 | 0.0206 | 0.0203 | 0.0204 | 0.0203 | 0.0192 | 0.0184 |
| −60.0 | 0.0210 | 0.0201 | 0.0203 | 0.0199 | 0.0193 | 0.0184 |
| −56.0 | 0.0219 | 0.0203 | 0.0208 | 0.0201 | 0.0197 | 0.0185 |
| −50.0 | 0.0251 | 0.0217 | 0.0221 | 0.0218 | 0.0212 | 0.0203 |
| −46.0 | 0.0307 | 0.0243 | 0.0247 | 0.0241 | 0.0234 | 0.0230 |
| −39.9 | 0.0596 | 0.0354 | 0.0352 | 0.0351 | 0.0340 | 0.0343 |
| −38.0 | 0.0871 | 0.0441 | 0.0440 | 0.0438 | 0.0433 | 0.0445 |
| −36.0 | 0.1387 | 0.0611 | 0.0608 | 0.0609 | 0.0604 | 0.0618 |
| −29.9 | 0.5029 | 0.2301 | 0.2320 | 0.2307 | 0.2349 | 0.2428 |
| −25.9 | 0.7660 | 0.5030 | 0.5065 | 0.5045 | 0.5266 | 0.5436 |
| −19.9 | 0.6480 | 0.8217 | 0.8347 | 0.8394 | 0.9297 | 0.9661 |
| −15.8 | 0.4673 | 0.7040 | 0.7229 | 0.7339 | 0.8344 | 0.8648 |
| −10.0 | 0.2975 | 0.4604 | 0.4786 | 0.4917 | 0.5750 | 0.5940 |
| −4.9 | 0.4017 | 0.5132 | 0.5310 | 0.5312 | 0.5719 | 0.5716 |
| 0.2 | 0.3409 | 0.4068 | 0.4188 | 0.4149 | 0.4338 | 0.4292 |
| 5.1 | 0.3017 | 0.3322 | 0.3379 | 0.3285 | 0.3322 | 0.3210 |
| 10.2 | 0.2797 | 0.2841 | 0.2868 | 0.2741 | 0.2622 | 0.2516 |
| 15.2 | 0.2694 | 0.2565 | 0.2557 | 0.2397 | 0.2200 | 0.2097 |
| 20.1 | 0.2637 | 0.2398 | 0.2378 | 0.2198 | 0.1942 | 0.1834 |

TABLE 7a-continued

Results (tan δ) of temperature sweep testing, Examples 24-29

| Temp. (° C.) | 24 | 25 | 26 | 27 | 28 | 29 |
|---|---|---|---|---|---|---|
| 25.2 | 0.2604 | 0.2303 | 0.2259 | 0.2061 | 0.1763 | 0.1661 |
| 30.2 | 0.2598 | 0.2230 | 0.2172 | 0.1972 | 0.1638 | 0.1542 |
| 35.2 | 0.2585 | 0.2182 | 0.2103 | 0.1894 | 0.1549 | 0.1433 |
| 40.2 | 0.2582 | 0.2134 | 0.2022 | 0.1805 | 0.1455 | 0.1336 |
| 45.3 | 0.2544 | 0.2064 | 0.1962 | 0.1743 | 0.1364 | 0.1263 |
| 50.1 | 0.2502 | 0.2005 | 0.1910 | 0.1668 | 0.1293 | 0.1195 |
| 55.1 | 0.2469 | 0.1942 | 0.1845 | 0.1607 | 0.1239 | 0.1130 |
| 60.1 | 0.2436 | 0.1886 | 0.1795 | 0.1563 | 0.1186 | 0.1102 |
| 65.2 | 0.2402 | 0.1843 | 0.1745 | 0.1515 | 0.1144 | 0.1061 |
| 70.2 | 0.2377 | 0.1793 | 0.1695 | 0.1466 | 0.1102 | 0.1027 |
| 75.3 | 0.2349 | 0.1756 | 0.1652 | 0.1428 | 0.1066 | 0.1009 |
| 80.2 | 0.2310 | 0.1714 | 0.1611 | 0.1383 | 0.1029 | 0.0963 |
| 85.3 | 0.2288 | 0.1671 | 0.1573 | 0.1346 | 0.0998 | 0.0933 |
| 90.3 | 0.2256 | 0.1631 | 0.1543 | 0.1306 | 0.0958 | 0.0909 |
| 95.3 | 0.2212 | 0.1578 | 0.1494 | 0.1270 | 0.0923 | 0.0873 |
| 100.3 | 0.2154 | 0.1543 | 0.1457 | 0.1220 | 0.0890 | 0.0840 |

TABLE 7b

Results (tan δ) of temperature sweep testing, Examples 30-35

| Temp. (° C.) | 30 | 31 | 32 | 33 | 34 | 35 |
|---|---|---|---|---|---|---|
| −80.1 | 0.0207 | 0.0222 | 0.0222 | 0.0225 | 0.0237 | 0.0222 |
| −76.0 | 0.0201 | 0.0214 | 0.0217 | 0.0217 | 0.0219 | 0.0215 |
| −70.0 | 0.0212 | 0.0217 | 0.0222 | 0.0222 | 0.0218 | 0.0221 |
| −66.0 | 0.0229 | 0.0229 | 0.0235 | 0.0234 | 0.0230 | 0.0235 |
| −59.9 | 0.0292 | 0.0310 | 0.0316 | 0.0319 | 0.0305 | 0.0314 |
| −55.9 | 0.0407 | 0.0470 | 0.0481 | 0.0488 | 0.0462 | 0.0469 |
| −50.0 | 0.0751 | 0.0705 | 0.0713 | 0.0713 | 0.0724 | 0.0731 |
| −46.0 | 0.1060 | 0.0736 | 0.0741 | 0.0715 | 0.0767 | 0.0787 |
| −39.9 | 0.1808 | 0.0982 | 0.0991 | 0.0932 | 0.1026 | 0.1069 |
| −35.8 | 0.2895 | 0.1460 | 0.1481 | 0.1388 | 0.1539 | 0.1603 |
| −29.9 | 0.6145 | 0.3299 | 0.3331 | 0.3228 | 0.3492 | 0.3590 |
| −25.9 | 0.7844 | 0.5659 | 0.5682 | 0.5518 | 0.5960 | 0.6013 |
| −19.9 | 0.5886 | 0.7849 | 0.7916 | 0.7968 | 0.9076 | 0.8919 |
| −15.9 | 0.4257 | 0.6446 | 0.6612 | 0.6824 | 0.8307 | 0.8058 |
| −9.8 | 0.2770 | 0.4083 | 0.4272 | 0.4511 | 0.5812 | 0.5639 |
| −5.1 | 0.3345 | 0.4350 | 0.4509 | 0.4782 | 0.5412 | 0.5356 |
| −0.1 | 0.2752 | 0.3397 | 0.3525 | 0.3729 | 0.4003 | 0.4002 |
| 4.9 | 0.2363 | 0.2750 | 0.2846 | 0.2983 | 0.2998 | 0.3038 |
| 9.8 | 0.2134 | 0.2317 | 0.2391 | 0.2472 | 0.2325 | 0.2370 |
| 14.9 | 0.1999 | 0.2037 | 0.2095 | 0.2144 | 0.1879 | 0.1937 |
| 19.9 | 0.1899 | 0.1849 | 0.1891 | 0.1908 | 0.1576 | 0.1635 |
| 24.8 | 0.1838 | 0.1701 | 0.1739 | 0.1732 | 0.1373 | 0.1412 |
| 29.9 | 0.1784 | 0.1607 | 0.1617 | 0.1616 | 0.1224 | 0.1237 |
| 34.9 | 0.1748 | 0.1521 | 0.1529 | 0.1507 | 0.1086 | 0.1108 |
| 39.7 | 0.1698 | 0.1449 | 0.1441 | 0.1422 | 0.0985 | 0.0980 |
| 44.7 | 0.1637 | 0.1366 | 0.1354 | 0.1329 | 0.0903 | 0.0892 |
| 49.7 | 0.1581 | 0.1302 | 0.1283 | 0.1251 | 0.0817 | 0.0821 |
| 54.7 | 0.1520 | 0.1238 | 0.1221 | 0.1190 | 0.0774 | 0.0747 |
| 59.5 | 0.1486 | 0.1189 | 0.1169 | 0.1141 | 0.0742 | 0.0714 |
| 64.5 | 0.1439 | 0.1144 | 0.1129 | 0.1095 | 0.0708 | 0.0671 |
| 69.5 | 0.1400 | 0.1106 | 0.1091 | 0.1063 | 0.0676 | 0.0643 |
| 74.4 | 0.1363 | 0.1062 | 0.1053 | 0.1021 | 0.0648 | 0.0619 |
| 79.5 | 0.1321 | 0.1029 | 0.1016 | 0.0983 | 0.0624 | 0.0593 |
| 84.5 | 0.1288 | 0.0999 | 0.0980 | 0.0953 | 0.0600 | 0.0565 |
| 89.4 | 0.1255 | 0.0975 | 0.0950 | 0.0923 | 0.0577 | 0.0553 |
| 94.4 | 0.1226 | 0.0941 | 0.0923 | 0.0900 | 0.0557 | 0.0528 |
| 100.4 | 0.1195 | 0.0911 | 0.0897 | 0.0871 | 0.0537 | 0.0509 |

That which is claimed is:

1. A process of making a functionalized polymer comprising polyene mer and at least one unit having the general formula

[chemical structure: a phenyl ring substituted with a C(CH₃)(CH₂—) group and (OH)$_m$ groups]

where m is an integer of from 2 to 5 inclusive, said process comprising anionically initiating polymerization of at least one type of polyene and a compound having the general formula

[chemical structure: a phenyl ring substituted with a C(CH₃)(=CH₂) group and (OG$_p$)$_m$ groups]

where each $G_p$ independently is a protecting group.

2. The process of claim 1 wherein said at least one type of polyene is polymerized before said compound is polymerized.

3. The process of claim 2 further comprising hydrolyzing each of said protecting groups so as to provide hydroxyl groups.

4. The process of claim 3 wherein m is 2.

5. The process of claim 4 wherein the two OG$_p$ groups are bonded to adjacent ring C atoms of the phenyl group.

6. The process of claim 2 wherein m is 2.

7. The process of claim 6 wherein the two OG$_p$ groups are bonded to adjacent ring C atoms of the phenyl group.

8. The process of claim 1 further comprising hydrolyzing each of said protecting groups so as to provide hydroxyl groups.

9. The process of claim 8 wherein m is 2.

10. The process of claim 9 wherein the two OG$_p$ groups are bonded to adjacent ring C atoms of the phenyl group.

11. The process of claim 1 wherein m is 2.

12. The process of claim 11 wherein the two OG$_p$ groups are bonded to adjacent ring C atoms of the phenyl group.

13. The process of claim 1 wherein each $G_p$ is a trialkylsilyl halide.

14. The process of claim 1 further comprising recovering and isolating and blending said polymer with ingredients that comprise at least one particulate filler so as to provide a rubber composition.

15. The process of claim 14 wherein said at least one particulate filler comprises carbon black.

16. The process of claim 15 wherein said rubber composition further comprises a vulcanizing agent.

17. The process of claim 16 further comprising vulcanizing said rubber composition so as to provide a vulcanizate, said vulcanizate optionally being a tire component.

18. The process of claim 15 wherein said at least one particulate filler further comprises silica.

19. The process of claim 18 wherein said rubber composition further comprises a vulcanizing agent.

20. The process of claim 19 further comprising vulcanizing said rubber composition so as to provide a vulcanizate, said vulcanizate optionally being a tire component.

* * * * *